US012788988B2

(12) United States Patent
Steinke et al.

(10) Patent No.: US 12,788,988 B2
(45) Date of Patent: Nov. 10, 2026

(54) SYSTEMS AND METHODS FOR MODIFYING STIMULATION IN RESPONSE TO A CHANGE IN A SYMPTOM, THERAPEUTIC EFFECT, OR SIDE EFFECT

(71) Applicant: Boston Scientific Neuromodulation Corporation, Valencia, CA (US)

(72) Inventors: G. Karl Steinke, Valencia, CA (US); Lisa Denise Moore, Glendale, CA (US); Mahsa Malekmohammadi, Sherman Oaks, CA (US)

(73) Assignee: Boston Scientific Neuromodulation Corporation, Valencia, CA (US)

( * ) Notice: Subject to any disclaimer, the term of this patent is extended or adjusted under 35 U.S.C. 154(b) by 208 days.

(21) Appl. No.: 18/645,034

(22) Filed: Apr. 24, 2024

(65) Prior Publication Data

US 2024/0359015 A1 Oct. 31, 2024

Related U.S. Application Data

(60) Provisional application No. 63/462,905, filed on Apr. 28, 2023.

(51) Int. Cl.
*A61N 1/36* (2006.01)

(52) U.S. Cl.
CPC ...... *A61N 1/36132* (2013.01); *A61N 1/36139* (2013.01)

(58) Field of Classification Search
CPC ............ A61N 1/36139; A61N 1/36132; A61N 1/36128
See application file for complete search history.

(56) References Cited

U.S. PATENT DOCUMENTS 3,999,555 A 12/1976 Person
4,144,889 A 3/1979 Tyers et al.
(Continued)

FOREIGN PATENT DOCUMENTS

EP 0813889 12/1997
EP 1048320 11/2000
(Continued)

OTHER PUBLICATIONS

Zhang, Y., et al., "Atlas-guided tract reconstruction for automated and comprehensive examination of the white matter anatomy," Neuroimage 52(4) (2010), pp. 1289-1301.
(Continued)

*Primary Examiner* — Catherine M Voorhees
(74) *Attorney, Agent, or Firm* — Branch Partners PLLC; Bruce E. Black

(57) ABSTRACT

A method for adapting stimulation by a stimulation system to a change in a symptom, therapeutic effect, or side effect includes detecting a change in a symptom of a disease or disorder or in a therapeutic effect or a side effect of stimulation by the stimulation system; in response to the detecting, determining, by the stimulation system, a modification of one or more stimulation parameter values to adapt to the change in the symptom, the therapeutic effect, or the side effect; and at least one of the following: 1) suggesting to the patient or to a clinician adoption of the modification and, upon receiving affirmation from the patient or the clinician, stimulating the patient according to the modification of the one or more stimulation parameter values, or 2) automatically stimulating the patient according to the modification of the one or more stimulation parameter values.

18 Claims, 6 Drawing Sheets

(56) References Cited

U.S. PATENT DOCUMENTS

| | | | |
|---|---|---|---|
| 4,177,818 | A | 12/1979 | De Pedro |
| 4,341,221 | A | 7/1982 | Testerman |
| 4,378,797 | A | 4/1983 | Osterholm |
| 4,445,500 | A | 5/1984 | Osterholm |
| 4,735,208 | A | 4/1988 | Wyler et al. |
| 4,765,341 | A | 8/1988 | Mower et al. |
| 4,841,973 | A | 6/1989 | Stecker |
| 5,067,495 | A | 11/1991 | Brehm |
| 5,099,846 | A | 3/1992 | Hardy |
| 5,222,494 | A | 6/1993 | Baker, Jr. |
| 5,255,693 | A | 10/1993 | Dutcher |
| 5,259,387 | A | 11/1993 | dePinto |
| 5,304,206 | A | 4/1994 | Baker, Jr. et al. |
| 5,344,438 | A | 9/1994 | Testerman et al. |
| 5,361,763 | A | 11/1994 | Kao et al. |
| 5,452,407 | A | 9/1995 | Crook |
| 5,560,360 | A | 10/1996 | Filler et al. |
| 5,565,949 | A | 10/1996 | Kasha, Jr. |
| 5,593,427 | A | 1/1997 | Gliner et al. |
| 5,601,612 | A | 2/1997 | Gliner et al. |
| 5,607,454 | A | 3/1997 | Cameron et al. |
| 5,620,470 | A | 4/1997 | Gliner et al. |
| 5,651,767 | A | 7/1997 | Schulman |
| 5,711,316 | A | 1/1998 | Elsberry et al. |
| 5,713,922 | A | 2/1998 | King |
| 5,716,377 | A | 2/1998 | Rise et al. |
| 5,724,985 | A | 3/1998 | Snell et al. |
| 5,749,904 | A | 5/1998 | Gliner et al. |
| 5,749,905 | A | 5/1998 | Gliner et al. |
| 5,776,170 | A | 7/1998 | MacDonald et al. |
| 5,782,762 | A | 7/1998 | Vining |
| 5,843,148 | A | 12/1998 | Gijsbers et al. |
| 5,859,922 | A | 1/1999 | Hoffmann |
| 5,868,740 | A | 2/1999 | LeVeen et al. |
| 5,897,583 | A | 4/1999 | Meyer et al. |
| 5,910,804 | A | 6/1999 | Fortenbery et al. |
| 5,925,070 | A | 7/1999 | King et al. |
| 5,938,688 | A | 8/1999 | Schiff |
| 5,938,690 | A | 8/1999 | Law et al. |
| 5,978,713 | A | 11/1999 | Prutchi et al. |
| 6,016,449 | A | 1/2000 | Fischell et al. |
| 6,029,090 | A | 2/2000 | Herbst |
| 6,029,091 | A | 2/2000 | de la Rama et al. |
| 6,050,992 | A | 4/2000 | Nichols |
| 6,058,331 | A | 5/2000 | King |
| 6,066,163 | A | 5/2000 | John |
| 6,080,187 | A | 6/2000 | Alt et al. |
| 6,083,162 | A | 7/2000 | Vining |
| 6,094,598 | A | 7/2000 | Elsberry et al. |
| 6,096,756 | A | 8/2000 | Crain et al. |
| 6,106,460 | A | 8/2000 | Panescu et al. |
| 6,109,269 | A | 8/2000 | Rise et al. |
| 6,128,538 | A | 10/2000 | Fischell et al. |
| 6,129,685 | A | 10/2000 | Howard, III |
| 6,146,390 | A | 11/2000 | Heilbrun et al. |
| 6,161,044 | A | 12/2000 | Silverstone |
| 6,167,311 | A | 12/2000 | Rezai |
| 6,181,969 | B1 | 1/2001 | Gord |
| 6,192,266 | B1 | 2/2001 | Dupree et al. |
| 6,205,361 | B1 | 3/2001 | Kuzma |
| 6,208,881 | B1 | 3/2001 | Champeau |
| 6,240,308 | B1 | 5/2001 | Hardy et al. |
| 6,246,912 | B1 | 6/2001 | Sluijter et al. |
| 6,253,109 | B1 | 6/2001 | Gielen |
| 6,289,239 | B1 | 9/2001 | Panescu et al. |
| 6,301,492 | B1 | 10/2001 | Zonenshayn |
| 6,310,619 | B1 | 10/2001 | Rice |
| 6,319,241 | B1 | 11/2001 | King |
| 6,336,899 | B1 | 1/2002 | Yamazaki |
| 6,343,226 | B1 | 1/2002 | Sunde et al. |
| 6,351,675 | B1 | 2/2002 | Tholen et al. |
| 6,353,762 | B1 | 3/2002 | Baudino et al. |
| 6,366,813 | B1 | 4/2002 | Dilorenzo |
| 6,368,331 | B1 | 4/2002 | Front et al. |
| 6,389,311 | B1 | 5/2002 | Whayne et al. |
| 6,393,325 | B1 | 5/2002 | Mann et al. |
| 6,421,566 | B1 | 7/2002 | Holsheimer |
| 6,435,878 | B1 | 8/2002 | Reynolds et al. |
| 6,442,432 | B2 | 8/2002 | Lee |
| 6,463,328 | B1 | 10/2002 | John |
| 6,491,699 | B1 | 12/2002 | Henderson et al. |
| 6,494,831 | B1 | 12/2002 | Koritzinsky |
| 6,507,759 | B1 | 1/2003 | Prutchi et al. |
| 6,510,347 | B2 | 1/2003 | Borkan |
| 6,516,227 | B1 | 2/2003 | Meadows et al. |
| 6,517,480 | B1 | 2/2003 | Krass |
| 6,539,263 | B1 | 3/2003 | Schiff |
| 6,560,490 | B2 | 5/2003 | Grill et al. |
| 6,579,280 | B1 | 6/2003 | Kovach et al. |
| 6,600,956 | B2 | 7/2003 | Maschino et al. |
| 6,606,523 | B1 | 8/2003 | Jenkins |
| 6,609,029 | B1 | 8/2003 | Mann et al. |
| 6,609,031 | B1 | 8/2003 | Law et al. |
| 6,609,032 | B1 | 8/2003 | Woods et al. |
| 6,622,048 | B1 | 9/2003 | Mann et al. |
| 6,631,297 | B1 | 10/2003 | Mo |
| 6,654,642 | B2 | 11/2003 | North et al. |
| 6,662,053 | B2 | 12/2003 | Borkan |
| 6,675,046 | B2 | 1/2004 | Holsheimer |
| 6,684,106 | B2 | 1/2004 | Herbst |
| 6,687,392 | B1 | 2/2004 | Touzawa et al. |
| 6,690,972 | B2 | 2/2004 | Conley et al. |
| 6,690,974 | B2 | 2/2004 | Archer et al. |
| 6,692,315 | B1 | 2/2004 | Soumillion et al. |
| 6,694,162 | B2 | 2/2004 | Hartlep |
| 6,694,163 | B1 | 2/2004 | Vining |
| 6,708,096 | B1 | 3/2004 | Frei et al. |
| 6,741,892 | B1 | 5/2004 | Meadows et al. |
| 6,748,098 | B1 | 6/2004 | Rosenfeld |
| 6,748,276 | B1 | 6/2004 | Daignault, Jr. et al. |
| 6,778,846 | B1 | 8/2004 | Martinez et al. |
| 6,788,969 | B2 | 9/2004 | Dupree et al. |
| 6,795,737 | B2 | 9/2004 | Gielen et al. |
| 6,827,681 | B2 | 12/2004 | Tanner et al. |
| 6,830,544 | B2 | 12/2004 | Tanner |
| 6,845,267 | B2 | 1/2005 | Harrison et al. |
| 6,850,802 | B2 | 2/2005 | Holsheimer |
| 6,895,280 | B2 | 5/2005 | Meadows et al. |
| 6,909,913 | B2 | 6/2005 | Vining |
| 6,937,891 | B2 | 8/2005 | Leinders et al. |
| 6,937,903 | B2 | 8/2005 | Schuler et al. |
| 6,944,497 | B2 | 9/2005 | Stypulkowski |
| 6,944,501 | B1 | 9/2005 | Pless |
| 6,950,707 | B2 | 9/2005 | Whitehurst |
| 6,969,388 | B2 | 11/2005 | Goldman et al. |
| 6,993,384 | B2 | 1/2006 | Bradley et al. |
| 7,003,349 | B1 | 2/2006 | Andersson et al. |
| 7,003,352 | B1 | 2/2006 | Whitehurst |
| 7,008,370 | B2 | 3/2006 | Tanner et al. |
| 7,008,413 | B2 | 3/2006 | Kovach et al. |
| 7,035,690 | B2 | 4/2006 | Goetz |
| 7,043,293 | B1 | 5/2006 | Baura |
| 7,047,082 | B1 | 5/2006 | Schrom et al. |
| 7,047,084 | B2 | 5/2006 | Erickson et al. |
| 7,050,857 | B2 | 5/2006 | Samuelsson et al. |
| 7,054,692 | B1 | 5/2006 | Whitehurst et al. |
| 7,058,446 | B2 | 6/2006 | Schuler et al. |
| 7,082,333 | B1 | 7/2006 | Bauhahn et al. |
| 7,107,102 | B2 | 9/2006 | Daignault et al. |
| 7,126,000 | B2 | 10/2006 | Ogawa et al. |
| 7,127,297 | B2 | 10/2006 | Law et al. |
| 7,136,518 | B2 | 11/2006 | Griffin et al. |
| 7,136,695 | B2 | 11/2006 | Pless et al. |
| 7,142,923 | B2 | 11/2006 | North et al. |
| 7,146,219 | B2 | 12/2006 | Sieracki et al. |
| 7,146,223 | B1 | 12/2006 | King |
| 7,151,961 | B1 | 12/2006 | Whitehurst |
| 7,155,279 | B2 | 12/2006 | Whitehurst |
| 7,167,760 | B2 | 1/2007 | Dawant et al. |
| 7,177,674 | B2 | 2/2007 | Echauz et al. |
| 7,181,286 | B2 | 2/2007 | Sieracki et al. |
| 7,184,837 | B2 | 2/2007 | Goetz |
| 7,191,014 | B2 | 3/2007 | Kobayashi et al. |
| 7,209,787 | B2 | 4/2007 | Dilorenzo |

(56) References Cited

U.S. PATENT DOCUMENTS 7,211,050 B1 5/2007 Caplygin
7,216,000 B2 5/2007 Sieracki et al.
7,217,276 B2 5/2007 Henderson
7,218,968 B2 5/2007 Condie et al.
7,228,179 B2 6/2007 Campen et al.
7,231,254 B2 6/2007 DiLorenzo
7,236,830 B2 6/2007 Gliner
7,239,910 B2 7/2007 Tanner
7,239,916 B2 7/2007 Thompson et al.
7,239,926 B2 7/2007 Goetz
7,242,984 B2 7/2007 DiLorenzo
7,244,150 B1 7/2007 Brase et al.
7,252,090 B2 8/2007 Goetz
7,254,445 B2 8/2007 Law et al.
7,254,446 B1 8/2007 Erickson
7,257,447 B2 8/2007 Cates et al.
7,266,412 B2 9/2007 Stypulkowski
7,289,761 B2 10/2007 Mazar
7,294,107 B2 11/2007 Simon et al.
7,295,876 B1 11/2007 Erickson
7,299,096 B2 11/2007 Balzer et al.
7,308,302 B1 12/2007 Schuler et al.
7,313,430 B2 12/2007 Urquhart
7,324,851 B1 1/2008 DiLorenzo
7,346,282 B2 3/2008 Sakanaka et al.
7,346,382 B2 3/2008 McIntyre et al.
7,385,443 B1 6/2008 Denison
7,388,974 B2 6/2008 Yanagita
7,437,193 B2 10/2008 Parramon et al.
7,450,997 B1 11/2008 Pianca et al.
7,454,245 B2 11/2008 Armstrong et al.
7,463,928 B2 12/2008 Lee et al.
7,499,048 B2 3/2009 Sieracki et al.
7,505,815 B2 3/2009 Lee et al.
7,548,786 B2 6/2009 Lee et al.
7,565,199 B2 7/2009 Sheffield et al.
7,603,177 B2 10/2009 Sieracki et al.
7,617,002 B2 11/2009 Goetz
7,623,918 B2 11/2009 Goetz
7,650,184 B2 1/2010 Walter
7,657,319 B2 2/2010 Goetz et al.
7,672,734 B2 3/2010 Anderson et al.
7,676,273 B2 3/2010 Goetz et al.
7,680,526 B2 3/2010 McIntyre et al.
7,734,340 B2 6/2010 De Ridder
7,761,165 B1 7/2010 He et al.
7,783,359 B2 8/2010 Meadows
7,792,590 B1 9/2010 Pianca et al.
7,809,446 B2 10/2010 Meadows
7,826,902 B2 11/2010 Stone et al.
7,848,802 B2 12/2010 Goetz et al.
7,860,548 B2 12/2010 McIntyre et al.
7,896,808 B1 3/2011 Koh et al.
7,904,134 B2 3/2011 McIntyre et al.
7,945,105 B1 5/2011 Jaenisch
7,949,395 B2 5/2011 Kuzma
7,974,706 B2 7/2011 Moffitt et al.
8,000,794 B2 8/2011 Lozano
8,019,439 B2 9/2011 Kuzma et al.
8,019,443 B2 9/2011 Schleicher et al.
8,175,710 B2 5/2012 He
8,180,601 B2 5/2012 Butson et al.
8,187,209 B1 5/2012 Giuffrida
8,195,300 B2 6/2012 Gliner et al.
8,209,027 B2 6/2012 Butson et al.
8,224,450 B2 7/2012 Brase
8,257,684 B2 9/2012 Covalin et al.
8,262,714 B2 9/2012 Hulvershorn et al.
8,271,094 B1 9/2012 Moffitt et al.
8,280,514 B2 10/2012 Lozano et al.
8,295,944 B2 10/2012 Howard et al.
8,306,627 B2 11/2012 Armstrong
8,311,639 B2 * 11/2012 Parker ................ A61N 1/36139
607/62
8,326,433 B2 12/2012 Blum et al.
8,359,107 B2 1/2013 Pianca et al.
8,364,278 B2 1/2013 Pianca et al.
8,369,954 B2 2/2013 Stack et al.
8,379,952 B2 2/2013 McIntyre et al.
8,391,985 B2 3/2013 McDonald
8,412,349 B2 4/2013 Barker
8,429,174 B2 4/2013 Ramani et al.
8,452,415 B2 5/2013 Goetz et al.
8,467,883 B2 6/2013 Chen et al.
8,473,061 B2 6/2013 Moffitt et al.
8,483,237 B2 7/2013 Zimmermann et al.
8,543,189 B2 9/2013 Paitel et al.
8,571,665 B2 10/2013 Moffitt et al.
8,589,316 B2 11/2013 Lujan et al.
8,594,800 B2 11/2013 Butson et al.
8,594,801 B2 11/2013 Corndorf et al.
8,606,360 B2 12/2013 Butson et al.
8,620,452 B2 12/2013 King et al.
8,649,845 B2 2/2014 McIntyre et al.
8,675,945 B2 3/2014 Barnhorst et al.
8,679,038 B1 3/2014 Giuffrida
8,688,235 B1 4/2014 Pianca et al.
8,744,596 B2 6/2014 Howard
8,751,008 B2 6/2014 Carlton et al.
8,751,016 B2 6/2014 Schleicher et al.
8,774,941 B2 7/2014 Pianca
8,792,993 B2 7/2014 Pianca et al.
8,831,731 B2 9/2014 Blum et al.
8,831,742 B2 9/2014 Pianca et al.
8,845,557 B1 9/2014 Giuffrida et al.
8,849,632 B2 9/2014 Sparks et al.
8,855,773 B2 10/2014 Kokones et al.
8,868,199 B2 10/2014 Kaula et al.
8,913,804 B2 12/2014 Blum et al.
8,918,183 B2 12/2014 Carlton et al.
8,918,184 B1 12/2014 Torgerson et al.
8,923,976 B2 12/2014 Johanek
8,936,622 B2 1/2015 Wales et al.
8,958,615 B2 2/2015 Blum et al.
8,972,023 B2 3/2015 Bradley et al.
8,986,382 B2 3/2015 Bentley et al.
9,020,789 B2 4/2015 Butson et al.
9,026,317 B2 5/2015 Furukawa et al.
9,039,740 B2 5/2015 Wales et al.
9,050,470 B2 6/2015 Carlton et al.
9,061,138 B2 6/2015 Pianca
9,072,905 B2 7/2015 Kokones et al.
9,081,488 B2 7/2015 Soederstroem
9,084,896 B2 7/2015 Kokones et al.
9,135,400 B2 9/2015 McIntyre et al.
9,149,630 B2 10/2015 Howard et al.
9,162,056 B2 10/2015 Pianca
9,220,889 B2 12/2015 Carlton et al.
9,227,074 B2 1/2016 Carcieri et al.
9,235,685 B2 1/2016 McIntyre et al.
9,248,272 B2 2/2016 Romero
9,248,296 B2 2/2016 Carcieri et al.
9,254,387 B2 2/2016 Blum et al.
9,272,153 B2 3/2016 Blum et al.
9,289,596 B2 3/2016 Leven
9,289,600 B2 3/2016 Govea et al.
9,302,110 B2 4/2016 Kokones et al.
9,308,372 B2 4/2016 Sparks et al.
9,310,985 B2 4/2016 Blum et al.
9,327,111 B2 5/2016 Pianca et al.
9,358,398 B2 6/2016 Moffitt et al.
9,364,665 B2 6/2016 Bokil et al.
9,381,348 B2 7/2016 Romero et al.
9,387,325 B1 7/2016 Min et al.
9,415,154 B2 8/2016 Leven et al.
9,474,903 B2 10/2016 Chen et al.
9,492,655 B2 11/2016 Pianca et al.
9,498,620 B2 11/2016 Romero et al.
9,526,902 B2 12/2016 Blum et al.
9,533,141 B2 1/2017 Black et al.
9,566,596 B2 2/2017 Kim et al.
9,572,982 B2 2/2017 Burnes et al.
9,586,053 B2 3/2017 Moffitt et al.
9,592,389 B2 3/2017 Moffitt

(56) References Cited

U.S. PATENT DOCUMENTS 9,610,435 B2 4/2017 Schleicher et al.
9,636,498 B2 5/2017 Leven
9,649,489 B2 5/2017 Wechter et al.
9,669,210 B2 6/2017 Barker et al.
9,713,720 B2 7/2017 Zhu
9,775,988 B2 10/2017 Govea et al.
9,792,412 B2 10/2017 Moffitt et al.
9,821,167 B2 11/2017 Carcieri et al.
9,887,470 B2 2/2018 Nguyen-Stella et al.
9,925,382 B2 3/2018 Carlton et al.
9,959,940 B2 5/2018 Moffitt et al.
9,974,959 B2 5/2018 Moffitt et al.
9,987,482 B2 6/2018 Nageri et al.
10,067,659 B2 9/2018 Bokil
10,071,242 B2 9/2018 Leven
10,071,249 B2 9/2018 Zottola
10,086,205 B2 10/2018 Grill et al.
10,213,148 B2 2/2019 Min et al.
10,226,616 B2 3/2019 Barker
10,265,528 B2 4/2019 Carcieri et al.
10,265,531 B2 4/2019 Bokil
10,286,205 B2 5/2019 Steinke et al.
10,300,282 B2 5/2019 Torgerson et al.
10,335,607 B2 7/2019 Orinski
10,357,657 B2 7/2019 Moffitt et al.
10,369,364 B2 8/2019 Moffitt et al.
10,406,353 B2 9/2019 Wechter
10,485,969 B2 11/2019 Govea et al.
10,493,269 B2 12/2019 Stoffregen et al.
10,525,257 B2 1/2020 Govea et al.
10,525,266 B2 1/2020 Moffitt et al.
10,603,498 B2 3/2020 Blum et al.
10,625,072 B2 4/2020 Serrano Carmona
10,631,937 B2 4/2020 Tyulmankov et al.
10,639,488 B2 5/2020 Kalgren et al.
10,653,330 B2 5/2020 Angle et al.
10,675,468 B2 6/2020 Torgerson
10,709,886 B2 7/2020 Nagaoka et al.
10,716,505 B2 7/2020 Blum et al.
10,780,282 B2 9/2020 Mustakos et al.
10,814,127 B2 10/2020 Nageri et al.
10,814,140 B2 10/2020 Zhang et al.
10,835,739 B2 11/2020 Sandhu
10,850,101 B2 12/2020 Zhang et al.
10,857,351 B2 12/2020 Wang et al.
10,960,203 B2 3/2021 Tyler et al.
11,020,052 B2 6/2021 Zuckerman-Stark et al.
11,285,329 B2 3/2022 Carcieri et al.
11,298,550 B2 4/2022 Howard et al.
11,357,986 B2 6/2022 Steinke et al.
11,517,755 B2 12/2022 Zhang et al.
11,529,510 B2 12/2022 Leven
11,707,622 B2 7/2023 Juárez Paz
11,745,010 B2 9/2023 Donega et al.
2001/0031071 A1 10/2001 Nichols et al.
2002/0032375 A1 3/2002 Bauch et al.
2002/0062143 A1 5/2002 Baudino et al.
2002/0087201 A1 7/2002 Firlik et al.
2002/0099295 A1 7/2002 Gil et al.
2002/0115603 A1 8/2002 Whitehouse
2002/0116030 A1 8/2002 Rezei
2002/0123780 A1 9/2002 Grill et al.
2002/0128694 A1 9/2002 Holsheimer
2002/0151939 A1 10/2002 Rezai
2002/0183607 A1 12/2002 Bauch et al.
2002/0183740 A1 12/2002 Edwards et al.
2002/0183817 A1 12/2002 Van Venrooij et al.
2003/0097159 A1 5/2003 Schiff et al.
2003/0149450 A1 8/2003 Mayberg
2003/0171791 A1 9/2003 KenKnight et al.
2003/0212439 A1 11/2003 Schuler et al.
2004/0034394 A1 2/2004 Woods et al.
2004/0044279 A1 3/2004 Lewin et al.
2004/0044378 A1 3/2004 Holsheimer
2004/0044379 A1 3/2004 Holsheimer
2004/0054297 A1 3/2004 Wingeier et al.
2004/0059395 A1 3/2004 North et al.
2004/0106916 A1 6/2004 Quaid et al.
2004/0133248 A1 7/2004 Frei et al.
2004/0152957 A1 8/2004 Stivoric et al.
2004/0181262 A1 9/2004 Bauhahn
2004/0186532 A1 9/2004 Tadlock
2004/0193231 A1 9/2004 David et al.
2004/0199216 A1 10/2004 Lee et al.
2004/0267330 A1 12/2004 Lee et al.
2005/0021090 A1 1/2005 Schuler et al.
2005/0033380 A1 2/2005 Tanner et al.
2005/0049649 A1 3/2005 Luders et al.
2005/0060001 A1 3/2005 Singhal et al.
2005/0060009 A1 3/2005 Goetz
2005/0070781 A1 3/2005 Dawant et al.
2005/0075689 A1 4/2005 Toy et al.
2005/0085714 A1 4/2005 Foley et al.
2005/0165294 A1 7/2005 Weiss
2005/0171587 A1 8/2005 Daglow et al.
2005/0228250 A1 10/2005 Bitter et al.
2005/0251061 A1 11/2005 Schuler et al.
2005/0261061 A1 11/2005 Nguyen et al.
2005/0261601 A1 11/2005 Schuler et al.
2005/0261747 A1 11/2005 Schuler et al.
2005/0267347 A1 12/2005 Oster
2005/0288732 A1 12/2005 Schuler et al.
2006/0004422 A1 1/2006 De Ridder
2006/0017749 A1 1/2006 McIntyre et al.
2006/0020292 A1 1/2006 Goetz et al.
2006/0069415 A1 3/2006 Cameron et al.
2006/0094951 A1 5/2006 Dean et al.
2006/0095088 A1 5/2006 Riddler
2006/0155340 A1 7/2006 Schuler et al.
2006/0206169 A1 9/2006 Schuler
2006/0218007 A1 9/2006 Bjorner et al.
2006/0224189 A1 10/2006 Schuler et al.
2006/0235472 A1 10/2006 Goetz et al.
2006/0259079 A1 11/2006 King
2006/0259099 A1 11/2006 Goetz et al.
2007/0000372 A1 1/2007 Rezai et al.
2007/0017749 A1 1/2007 Dold et al.
2007/0027499 A1 2/2007 Maschino et al.
2007/0027514 A1 2/2007 Gerber
2007/0043268 A1 2/2007 Russell
2007/0049817 A1 3/2007 Preiss et al.
2007/0067003 A1 3/2007 Sanchez et al.
2007/0078498 A1 4/2007 Rezai et al.
2007/0083104 A1 4/2007 Butson et al.
2007/0123953 A1 5/2007 Lee et al.
2007/0129769 A1 6/2007 Bourget et al.
2007/0135855 A1 6/2007 Foshee et al.
2007/0150026 A1 6/2007 Bourget et al.
2007/0150036 A1 6/2007 Anderson
2007/0156186 A1 7/2007 Lee et al.
2007/0162086 A1 7/2007 DiLorenzo
2007/0162235 A1 7/2007 Zhan et al.
2007/0168004 A1 7/2007 Walter
2007/0168007 A1 7/2007 Kuzma et al.
2007/0179557 A1 8/2007 Maschino et al.
2007/0185544 A1 8/2007 Dawant et al.
2007/0191887 A1 8/2007 Schuler et al.
2007/0191912 A1 8/2007 Ficher et al.
2007/0197891 A1 8/2007 Shachar et al.
2007/0203450 A1 8/2007 Berry
2007/0203532 A1 8/2007 Tass et al.
2007/0203537 A1 8/2007 Goetz et al.
2007/0203538 A1 8/2007 Stone et al.
2007/0203539 A1 8/2007 Stone et al.
2007/0203540 A1 8/2007 Goetz et al.
2007/0203541 A1 8/2007 Goetz et al.
2007/0203543 A1 8/2007 Stone et al.
2007/0203544 A1 8/2007 Goetz et al.
2007/0203545 A1 8/2007 Stone et al.
2007/0203546 A1 8/2007 Stone et al.
2007/0213789 A1 9/2007 Nolan et al.
2007/0213790 A1 9/2007 Nolan et al.
2007/0244519 A1 10/2007 Keacher et al.
2007/0245318 A1 10/2007 Goetz et al.

(56) References Cited

U.S. PATENT DOCUMENTS

| | | | |
|---|---|---|---|
| 2007/0255321 | A1 | 11/2007 | Gerber et al. |
| 2007/0255322 | A1 | 11/2007 | Gerber et al. |
| 2007/0260283 | A1 | 11/2007 | Li |
| 2007/0265664 | A1 | 11/2007 | Gerber et al. |
| 2007/0276441 | A1 | 11/2007 | Goetz |
| 2007/0282189 | A1 | 12/2007 | Dan et al. |
| 2007/0288064 | A1 | 12/2007 | Butson et al. |
| 2008/0027514 | A1 | 1/2008 | DeMulling et al. |
| 2008/0039895 | A1 | 2/2008 | Fowler et al. |
| 2008/0046037 | A1 | 2/2008 | Haubrich et al. |
| 2008/0071150 | A1 | 3/2008 | Miesel et al. |
| 2008/0081982 | A1 | 4/2008 | Simon et al. |
| 2008/0086451 | A1 | 4/2008 | Torres et al. |
| 2008/0091248 | A1 | 4/2008 | Libbus et al. |
| 2008/0103533 | A1 | 5/2008 | Patel et al. |
| 2008/0114233 | A1 | 5/2008 | McIntyre et al. |
| 2008/0114579 | A1 | 5/2008 | McIntyre et al. |
| 2008/0123922 | A1 | 5/2008 | Gielen et al. |
| 2008/0123923 | A1 | 5/2008 | Gielen et al. |
| 2008/0133141 | A1 | 6/2008 | Frost |
| 2008/0141217 | A1 | 6/2008 | Goetz et al. |
| 2008/0154340 | A1 | 6/2008 | Goetz et al. |
| 2008/0154341 | A1 | 6/2008 | McIntyre et al. |
| 2008/0163097 | A1 | 7/2008 | Goetz et al. |
| 2008/0183256 | A1 | 7/2008 | Keacher |
| 2008/0188734 | A1 | 8/2008 | Suryanarayanan et al. |
| 2008/0215101 | A1 | 9/2008 | Rezai et al. |
| 2008/0215118 | A1 | 9/2008 | Goetz et al. |
| 2008/0227139 | A1 | 9/2008 | Deisseroth et al. |
| 2008/0238749 | A1 | 10/2008 | Comdorf |
| 2008/0242950 | A1 | 10/2008 | Jung et al. |
| 2008/0261165 | A1 | 10/2008 | Steingart et al. |
| 2008/0269588 | A1 | 10/2008 | Csavoy et al. |
| 2008/0300654 | A1 | 12/2008 | Lambert et al. |
| 2008/0300797 | A1 | 12/2008 | Tabibiazar et al. |
| 2009/0016491 | A1 | 1/2009 | Li |
| 2009/0054947 | A1 | 2/2009 | Bourn et al. |
| 2009/0054950 | A1 | 2/2009 | Stephens |
| 2009/0082640 | A1 | 3/2009 | Kovach et al. |
| 2009/0082829 | A1 | 3/2009 | Panken et al. |
| 2009/0112289 | A1 | 4/2009 | Lee et al. |
| 2009/0118635 | A1 | 5/2009 | Lujan et al. |
| 2009/0118786 | A1 | 5/2009 | Meadows et al. |
| 2009/0149917 | A1 | 6/2009 | Whitehurst et al. |
| 2009/0163975 | A1 | 6/2009 | Gerber et al. |
| 2009/0187222 | A1 | 7/2009 | Barker |
| 2009/0196471 | A1 | 8/2009 | Goetz et al. |
| 2009/0196472 | A1 | 8/2009 | Goetz et al. |
| 2009/0198306 | A1 | 8/2009 | Goetz et al. |
| 2009/0198354 | A1 | 8/2009 | Wilson |
| 2009/0204192 | A1 | 8/2009 | Carlton et al. |
| 2009/0208073 | A1 | 8/2009 | McIntyre et al. |
| 2009/0210208 | A1 | 8/2009 | McIntyre et al. |
| 2009/0228073 | A1 | 9/2009 | Scholten |
| 2009/0242399 | A1 | 10/2009 | Kamath et al. |
| 2009/0270949 | A1 | 10/2009 | Kalpin et al. |
| 2009/0276008 | A1 | 11/2009 | Lee et al. |
| 2009/0276021 | A1 | 11/2009 | Meadows et al. |
| 2009/0281595 | A1 | 11/2009 | King et al. |
| 2009/0281596 | A1 | 11/2009 | King et al. |
| 2009/0287271 | A1 | 11/2009 | Blum et al. |
| 2009/0287272 | A1 | 11/2009 | Kokones et al. |
| 2009/0287273 | A1 | 11/2009 | Carlton et al. |
| 2009/0287467 | A1 | 11/2009 | Sparks et al. |
| 2009/0299164 | A1 | 12/2009 | Singhal et al. |
| 2009/0299165 | A1 | 12/2009 | Singhal et al. |
| 2009/0299380 | A1 | 12/2009 | Singhal et al. |
| 2010/0010387 | A1 | 1/2010 | Skelton et al. |
| 2010/0010432 | A1 | 1/2010 | Skelton |
| 2010/0010566 | A1 | 1/2010 | Thacker et al. |
| 2010/0010646 | A1 | 1/2010 | Drew et al. |
| 2010/0023103 | A1 | 1/2010 | Elborno |
| 2010/0023130 | A1 | 1/2010 | Henry et al. |
| 2010/0030312 | A1 | 2/2010 | Shen |
| 2010/0049276 | A1 | 2/2010 | Blum et al. |
| 2010/0049280 | A1 | 2/2010 | Goetz |
| 2010/0057161 | A1 | 3/2010 | Machado et al. |
| 2010/0064249 | A1 | 3/2010 | Groetken |
| 2010/0076535 | A1 | 3/2010 | Pianca et al. |
| 2010/0113959 | A1 | 5/2010 | Pascual-Leon et al. |
| 2010/0121409 | A1 | 5/2010 | Kothandaraman et al. |
| 2010/0135553 | A1 | 6/2010 | Joglekar |
| 2010/0137944 | A1 | 6/2010 | Zhu |
| 2010/0152604 | A1 | 6/2010 | Kuala et al. |
| 2010/0152807 | A1 | 6/2010 | Grill et al. |
| 2010/0179562 | A1 | 7/2010 | Linker et al. |
| 2010/0211135 | A1 | 8/2010 | Caparso et al. |
| 2010/0268298 | A1 | 10/2010 | Moffitt |
| 2010/0324410 | A1 | 12/2010 | Paek et al. |
| 2010/0331883 | A1 | 12/2010 | Schmitz et al. |
| 2011/0004267 | A1 | 1/2011 | Meadows |
| 2011/0005069 | A1 | 1/2011 | Pianca |
| 2011/0040351 | A1 | 2/2011 | Buston et al. |
| 2011/0054559 | A1 | 3/2011 | Rosenberg et al. |
| 2011/0066407 | A1 | 3/2011 | Butson et al. |
| 2011/0078900 | A1 | 4/2011 | Pianca et al. |
| 2011/0093045 | A1 | 4/2011 | Moffitt |
| 2011/0130803 | A1 | 6/2011 | McDonald |
| 2011/0130816 | A1 | 6/2011 | Howard et al. |
| 2011/0130817 | A1 | 6/2011 | Chen |
| 2011/0130818 | A1 | 6/2011 | Chen |
| 2011/0137372 | A1 | 6/2011 | Makous et al. |
| 2011/0160796 | A1 | 6/2011 | Lane et al. |
| 2011/0172737 | A1 | 7/2011 | Davis et al. |
| 2011/0184487 | A1 | 7/2011 | Alberts et al. |
| 2011/0191275 | A1 | 8/2011 | Lujan et al. |
| 2011/0196253 | A1 | 8/2011 | McIntyre et al. |
| 2011/0213440 | A1 | 9/2011 | Fowler et al. |
| 2011/0224665 | A1 | 9/2011 | Crosby et al. |
| 2011/0224680 | A1 | 9/2011 | Barker |
| 2011/0238129 | A1 | 9/2011 | Moffitt |
| 2011/0251583 | A1 | 10/2011 | Miyazawa et al. |
| 2011/0270348 | A1 | 11/2011 | Goetz |
| 2011/0306845 | A1 | 12/2011 | Osorio |
| 2011/0306846 | A1 | 12/2011 | Osorio |
| 2011/0307032 | A1 | 12/2011 | Goetz et al. |
| 2011/0313485 | A1 | 12/2011 | DeMulling et al. |
| 2011/0313500 | A1 | 12/2011 | Barker et al. |
| 2012/0016378 | A1 | 1/2012 | Pianca et al. |
| 2012/0027272 | A1 | 2/2012 | Akinyemi et al. |
| 2012/0046710 | A1 | 2/2012 | Digiore et al. |
| 2012/0046715 | A1 | 2/2012 | Moffitt et al. |
| 2012/0071949 | A1 | 3/2012 | Pianca et al. |
| 2012/0078106 | A1 | 3/2012 | Dentinger et al. |
| 2012/0089205 | A1 | 4/2012 | Boyden et al. |
| 2012/0101552 | A1 | 4/2012 | Lazarewicz et al. |
| 2012/0116476 | A1 | 5/2012 | Kothandaraman |
| 2012/0165898 | A1 | 6/2012 | Moffitt |
| 2012/0165901 | A1 | 6/2012 | Zhu et al. |
| 2012/0165911 | A1 | 6/2012 | Pianca |
| 2012/0197375 | A1 | 8/2012 | Pianca et al. |
| 2012/0203316 | A1 | 8/2012 | Moffitt et al. |
| 2012/0203320 | A1 | 8/2012 | Digiore et al. |
| 2012/0203321 | A1 | 8/2012 | Moffitt et al. |
| 2012/0207378 | A1 | 8/2012 | Gupta et al. |
| 2012/0226138 | A1 | 9/2012 | DeSalles et al. |
| 2012/0229468 | A1 | 9/2012 | Lee et al. |
| 2012/0239109 | A1 | 9/2012 | Lee |
| 2012/0239115 | A1 | 9/2012 | Lee |
| 2012/0265103 | A1 | 10/2012 | Policker et al. |
| 2012/0265262 | A1 | 10/2012 | Osorio |
| 2012/0265268 | A1 | 10/2012 | Blum et al. |
| 2012/0271189 | A1 | 10/2012 | Nelson et al. |
| 2012/0277833 | A1 | 11/2012 | Gerber et al. |
| 2012/0302912 | A1 | 11/2012 | Moffitt et al. |
| 2012/0303087 | A1 | 11/2012 | Moffitt et al. |
| 2012/0303098 | A1 | 11/2012 | Perryman |
| 2012/0314919 | A1 | 12/2012 | Sparks et al. |
| 2012/0314924 | A1 | 12/2012 | Carlton et al. |
| 2012/0316615 | A1 | 12/2012 | Digiore et al. |
| 2012/0316619 | A1 | 12/2012 | Goetz et al. |
| 2012/0330374 | A1 | 12/2012 | Blum et al. |
| 2012/0330622 | A1 | 12/2012 | Butson et al. |
| 2013/0035740 | A1 | 2/2013 | Sharma et al. |

(56) References Cited

U.S. PATENT DOCUMENTS

2013/0039550 A1 2/2013 Blum et al.
2013/0053926 A1 2/2013 Hincapie Ordonez et al.
2013/0060305 A1 3/2013 Bokil
2013/0105071 A1 5/2013 Digiore et al.
2013/0116744 A1 5/2013 Blum et al.
2013/0116748 A1 5/2013 Bokil et al.
2013/0116749 A1 5/2013 Carlton et al.
2013/0116929 A1 5/2013 Carlton et al.
2013/0150922 A1 6/2013 Butson et al.
2013/0197424 A1 8/2013 Bedenbaugh
2013/0197602 A1 8/2013 Pianca et al.
2013/0226261 A1 8/2013 Sparks et al.
2013/0245722 A1 9/2013 Ternes et al.
2013/0261684 A1 10/2013 Howard
2013/0289380 A1 10/2013 Molnar et al.
2013/0289660 A1 10/2013 Molnar et al.
2013/0317572 A1 11/2013 Zhu et al.
2013/0317573 A1 11/2013 Zhu et al.
2013/0317587 A1 11/2013 Barker
2013/0325091 A1 12/2013 Pianca et al.
2014/0039586 A1 2/2014 Barker et al.
2014/0039587 A1 2/2014 Romero
2014/0063017 A1 3/2014 Kaula et al.
2014/0066999 A1 3/2014 Carcieri et al.
2014/0067018 A1 3/2014 Carcieri et al.
2014/0067022 A1 3/2014 Carcieri et al.
2014/0074180 A1* 3/2014 Heldman ........... A61N 1/36067 607/45
2014/0081366 A1 3/2014 Bentley et al.
2014/0107731 A1 4/2014 Stone et al.
2014/0122379 A1 5/2014 Moffitt et al.
2014/0200633 A1 7/2014 Moffitt
2014/0243926 A1 8/2014 Carcieri
2014/0276707 A1 9/2014 Jaax
2014/0276927 A1 9/2014 Barker
2014/0277282 A1 9/2014 Jaax
2014/0277284 A1 9/2014 Chen et al.
2014/0296953 A1 10/2014 Pianca et al.
2014/0343647 A1 11/2014 Romero et al.
2014/0353001 A1 12/2014 Romero et al.
2014/0358207 A1 12/2014 Romero
2014/0358208 A1 12/2014 Howard et al.
2014/0358209 A1 12/2014 Romero et al.
2014/0358210 A1 12/2014 Howard et al.
2015/0018915 A1 1/2015 Leven
2015/0021817 A1 1/2015 Romero et al.
2015/0045864 A1 2/2015 Howard
2015/0051681 A1 2/2015 Hershey
2015/0066111 A1 3/2015 Blum et al.
2015/0066120 A1 3/2015 Govea
2015/0073431 A1 3/2015 Barker
2015/0073432 A1 3/2015 Barker
2015/0134031 A1 5/2015 Moffitt et al.
2015/0151113 A1 6/2015 Govea et al.
2015/0246231 A1 9/2015 Martens et al.
2015/0360039 A1 12/2015 Lempka et al.
2016/0001087 A1 1/2016 Moffitt
2016/0008632 A1 1/2016 Wetmore et al.
2016/0022995 A1 1/2016 Kothandaraman et al.
2016/0023008 A1 1/2016 Kothandaraman
2016/0030749 A1 2/2016 Carcieri et al.
2016/0030750 A1 2/2016 Bokil et al.
2016/0045748 A1 2/2016 Astrom et al.
2016/0082252 A1 3/2016 Hershey et al.
2016/0096025 A1 4/2016 Moffitt et al.
2016/0136429 A1 5/2016 Massoumi et al.
2016/0136443 A1 5/2016 Kothandaraman et al.
2016/0144186 A1 5/2016 Kaemmerer et al.
2016/0175594 A1 6/2016 Min et al.
2016/0206380 A1 7/2016 Sparks et al.
2016/0228692 A1 8/2016 Steinke et al.
2016/0256691 A1 9/2016 Cecchi et al.
2016/0256693 A1 9/2016 Parramon
2016/0317800 A1 11/2016 Barker
2016/0346557 A1 12/2016 Bokil
2016/0375248 A1 12/2016 Carcieri et al.
2016/0375258 A1 12/2016 Steinke
2017/0100593 A1 4/2017 Zottola
2017/0100601 A1 4/2017 Xiao et al.
2017/0106197 A1 4/2017 Wechter et al.
2017/0197086 A1 7/2017 Howard et al.
2017/0225007 A1 8/2017 Orinski
2017/0252570 A1 9/2017 Serrano Carmona et al.
2017/0259078 A1 9/2017 Howard
2017/0304610 A1 10/2017 Huibregtse et al.
2017/0304633 A1 10/2017 Zhang
2017/0372039 A1 12/2017 Mustakos et al.
2018/0064930 A1 3/2018 Zhang et al.
2018/0078776 A1 3/2018 Mustakos et al.
2018/0104482 A1 4/2018 Bokil
2018/0104500 A1 4/2018 Blum et al.
2018/0110971 A1 4/2018 Serrano Carmona
2018/0133481 A1 5/2018 Von Zitzewitz et al.
2018/0185650 A1 7/2018 Shah
2018/0193655 A1 7/2018 Zhang et al.
2018/0214700 A1 8/2018 Vansickle et al.
2018/0264278 A1 9/2018 Laghi
2018/0272142 A1 9/2018 Zhang et al.
2018/0280698 A1 10/2018 Steinke et al.
2018/0296828 A1 10/2018 Bradley et al.
2018/0333173 A1 11/2018 Wang
2018/0369589 A1 12/2018 Schouenborg et al.
2018/0369606 A1 12/2018 Zhang et al.
2018/0369607 A1 12/2018 Zhang et al.
2019/0015660 A1 1/2019 Zhang et al.
2019/0105503 A1 4/2019 Leven
2019/0184171 A1 6/2019 Mustakos et al.
2019/0209834 A1 7/2019 Zhang et al.
2019/0209849 A1 7/2019 Hershey et al.
2019/0262609 A1 8/2019 Brill et al.
2019/0275331 A1 9/2019 Zhu
2019/0329047 A1 10/2019 Moffitt et al.
2019/0329049 A1 10/2019 Carcieri et al.
2020/0094047 A1 3/2020 Govea et al.
2020/0139127 A1 5/2020 Zhang et al.
2020/0155854 A1 5/2020 Leven et al.
2020/0155859 A1 5/2020 Blum et al.
2020/0171298 A1 6/2020 Goetz et al.
2020/0171310 A1 6/2020 Walter et al.
2020/0179600 A1 6/2020 Zanos et al.
2020/0215330 A1 7/2020 Huertas Fernandez et al.
2020/0222704 A1 7/2020 Moffitt et al.
2020/0269053 A1 8/2020 Park
2020/0353254 A1 11/2020 OLaighin et al.
2020/0376262 A1 12/2020 Clark et al.
2020/0376263 A1 12/2020 Zhu
2020/0398057 A1 12/2020 Esteller et al.
2021/0008388 A1 1/2021 Vansickle et al.
2021/0008389 A1 1/2021 Featherstone et al.
2021/0016111 A1 1/2021 Vansickle et al.
2021/0023374 A1 1/2021 Block et al.
2021/0052893 A1 2/2021 Suri et al.
2021/0113844 A1 4/2021 Zhang et al.
2021/0128920 A1 5/2021 Grill et al.
2021/0196956 A1 7/2021 Juárez Paz
2021/0196964 A1* 7/2021 Schnell .................. A61B 5/372
2021/0205613 A1 7/2021 Bradley et al.
2021/0268268 A1 9/2021 Horn et al.
2021/0275820 A1 9/2021 Grill, Jr. et al.
2021/0387002 A1 12/2021 Bourget et al.
2022/0007980 A1 1/2022 Single
2022/0008729 A1 1/2022 Zhu
2022/0040485 A1 2/2022 Li et al.
2022/0062640 A1 3/2022 Raike et al.
2022/0072329 A1 3/2022 Howard
2022/0111213 A1 4/2022 Cassar et al.
2022/0126100 A1 4/2022 Jackson et al.
2022/0176118 A1* 6/2022 John .................. A61N 1/36017
2022/0257950 A1 8/2022 Moore et al.
2022/0266026 A1 8/2022 Case et al.
2022/0296892 A1 9/2022 Esteller et al.
2022/0296893 A1 9/2022 Steinke et al.
2022/0339448 A1 10/2022 Jayakumar et al.
2022/0347479 A1 11/2022 Esteller et al.

(56) References Cited

U.S. PATENT DOCUMENTS

| | | | |
|---|---|---|---|
| 2022/0355114 | A1 | 11/2022 | Moore et al. |
| 2022/0355115 | A1 | 11/2022 | Moore et al. |
| 2022/0370808 | A1 | 11/2022 | Esteller |
| 2022/0387785 | A1 | 12/2022 | Huynh et al. |
| 2022/0395690 | A1 | 12/2022 | Haddock et al. |
| 2023/0048571 | A1 | 2/2023 | Poltorak |
| 2023/0064552 | A1 | 3/2023 | Moffitt |
| 2023/0141183 | A1 | 5/2023 | Moore et al. |
| 2023/0181089 | A1 | 6/2023 | Zhang et al. |
| 2023/0181090 | A1 | 6/2023 | Juarez Paz |
| 2023/0181906 | A1 | 6/2023 | Moore et al. |
| 2023/0248977 | A1 | 8/2023 | Esteller et al. |
| 2023/0264025 | A1 | 8/2023 | Malekmohammadi |
| 2023/0271015 | A1 | 8/2023 | Malekmohammadi et al. |
| 2023/0277854 | A1 | 9/2023 | Gaviao Kilmar |
| 2024/0065620 | A1 | 2/2024 | Moore et al. |
| 2024/0157151 | A1 | 5/2024 | Juarez Paz |
| 2024/0198110 | A1 | 6/2024 | Moore |
| 2024/0316346 | A1 | 9/2024 | Shah et al. |
| 2024/0359015 | A1 | 10/2024 | Steinke et al. |
| 2025/0010079 | A1 | 1/2025 | Bokil |
| 2025/0050107 | A1 | 2/2025 | Moore et al. |

FOREIGN PATENT DOCUMENTS

| | | | |
|---|---|---|---|
| EP | 1166819 | | 1/2002 |
| EP | 1372780 | | 1/2004 |
| EP | 1559369 | | 8/2005 |
| WO | 97/39797 | | 10/1997 |
| WO | 98/48880 | | 11/1998 |
| WO | 01/90876 | | 11/2001 |
| WO | 02/26314 | | 4/2002 |
| WO | 02/28473 | | 4/2002 |
| WO | 02/065896 | | 8/2002 |
| WO | 02/072192 | | 9/2002 |
| WO | 03/086185 | | 10/2003 |
| WO | 2004/019799 | A2 | 3/2004 |
| WO | 2004041080 | | 5/2005 |
| WO | 2006017053 | | 2/2006 |
| WO | 2006113305 | | 10/2006 |
| WO | 20071097859 | | 8/2007 |
| WO | 20071097861 | A1 | 8/2007 |
| WO | 2007/100427 | | 9/2007 |
| WO | 2007/100428 | | 9/2007 |
| WO | 2007/112061 | | 10/2007 |
| WO | 2009097224 | | 8/2009 |
| WO | 2010/109448 | | 9/2010 |
| WO | 2010/120823 | A2 | 10/2010 |
| WO | 2011025865 | | 3/2011 |
| WO | 2011/139779 | A1 | 11/2011 |
| WO | 2011/159688 | A2 | 12/2011 |
| WO | 2012088482 | | 6/2012 |
| WO | 2016/025913 | | 2/2016 |
| WO | 2016081099 | | 5/2016 |
| WO | 2016112398 | | 7/2016 |

OTHER PUBLICATIONS

""BioPSE" The Biomedical Problem Solving Environment", htt12://www.sci.utah.edu/cibc/software/index.html, MCRR Center for Integrative Biomedical Computing, (2004).

Andrews, R. J., "Neuroprotection trek—the next generation: neuromodulation I. Techniques—deep brain stimulation, vagus nerve stimulation, and transcranial magnetic stimulation.", Ann NY Acad Sci. 993. (May 2003), 1-13.

Carnevale, N.T et al., "The Neuron Book," Cambridge, UK: Cambridge University Press (2006), 480 pages.

Chaturvedi: "Development of Accurate Computational Models for Patient-Specific Deep Brain Stimulation," Electronic Thesis or Dissertation, Jan. 2012, 162 pages.

Chaturvedi, A. et al.: "Patient-specific models of deep brain stimulation: Influence of field model complexity on neural activation predictions." Brain Stimulation, Elsevier, Amsterdam, NL, vol. 3, No. 2 Apr. 2010, pp. 65-77.

Frankemolle, et al., "Reversing cognitive-motor impairments in Parkinson's disease patients using a computational modeling approach to deep brain stimulation programming," Brian 133 (2010), pp. 746-761.

McIntyre, C.C., et al., "Modeling the excitablitity of mammalian nerve fibers: influence of afterpotentials on the recovery cycle," J Neurophysiol, 87(2) (Feb. 2002), pp. 995-1006.

Peterson, et al., "Predicting myelinated axon activation using spatial characteristics of the extracellular field," Journal of Neural Engineering, 8 (2011), 12 pages.

Warman, et al., "Modeling the Effects of Electric Fields on nerver Fibers; Dermination of Excitation Thresholds," IEEE Transactions on Biomedical Engineering, vol. 39, No. 12 (Dec. 1992), pp. 1244-1254.

Wesselink, et al., "Analysis of Current Density and Related Parameters in Spinal Cord Stimulation," IEEE Transactions on Rehabilitation Engineering, vol. 6, No. 2 Jun. 1998, pp. 200-207.

Andrews, R. J., "Neuroprotection trek—the next generation: neuromodulation II. Applications—epilepsy, nerve regeneration, neurotrophins.", Ann NY Acad Sci. 993 (May 2003), 14-24.

Astrom, M. , et al., "The effect of cystic cavities on deep brain stimulation in the basal ganglia: a simulation-based study", J Neural Eng., 3(2), (Jun. 2006). 132-8.

Bazin et al., "Free Software Tools for Atlas-based Volumetric Neuroimage Analysis", Proc. SPIE 5747, Medical Imaging 2005: Image Processing, 1824 May 5, 2005.

Back, C. , et al., "Postoperative Monitoring of the Electrical Properties of Tissue and Electrodes in Deep Brain Stimulation", Neuromodulation, 6(4), (Oct. 2003 ),248-253.

Baker, K. B., et al., "Evaluation of specific absorption rate as a dosimeter of MRI-related implant heating", J Magn Reson Imaging., 20(2), (Aug. 2004),315-20.

Brown, J. "Motor Cortex Stimulation," Neurosurgical Focus ( Sep. 15, 2001) 11(3):E5.

Budai et al., "Endogenous Opioid Peptides Acting at m-Opioid Receptors in the Dorsal Horn Contribute to Midbrain Modulation of Spinal Nociceptive Neurons," Journal of Neurophysiology (1998) 79(2): 677-687.

Cesselin, F. "Opioid and anti-opioid peptides," Fundamental and Clinical Pharmacology (1995) 9(5): 409-33 (Abstract only).

Rezai et al., "Deep Brain Stimulation for Chronic Pain" Surgical Management of Pain, Chapter 44 pp. 565-576 (2002).

Xu, Md., Shi-Ang, article entitled "Comparison of Half-Band and Full-Band Electrodes for Intracochlear Electrical Stimulation", Annals of Otology, Rhinology & Laryngology (Annals of Head & Neck Medicine & Surgery), vol. 102 (5) pp. 363-367 May 1993.

Bedard, C. , et al., "Modeling extracellular field potentials and the frequency-filtering properties of extracellular space", Biophys J . . . 86(3). (Mar. 2004), 1829-42.

Benabid, A. L., et al., "Future prospects of brain stimulation", Neurol Res.; 22(3), (Apr. 2000), 237-46.

Brummer, S. B., et al., "Electrical Stimulation with Pt Electrodes: II—Estimation of Maximum Surface Redox (Theoretical Non-Gassing) Limits", IEEE Transactions on Biomedical Engineering, vol. BME-24, Issue 5, (Sep. 1977), 440-443.

Butson, Christopher R., et al., "Deep Brain Stimulation of the Subthalamic Nucleus: Model-Based Analysis of the Effects of Electrode Capacitance on the Volume of Activation", Proceedings of the 2nd International IEEE EMBS, (Mar. 16-19, 2005), 196-197.

Mcintyre, Cameron C., et al., "Cellular effects of deep brain stimulation: model-based analysis of activation and inhibition," J Neurophysiol, 91(4) (Apr. 2004), pp. 1457-1469.

Chaturvedi, A., et al., "Subthalamic Nucleus Deep Brain Stimulation: Accurate Axonal Threshold Prediction with Diffusion Tensor Based Electric Field Models", Engineering in Medicine and Biology Society, 2006. EMBS' 06 28th Annual International Conference of the IEEE, IEEE, Piscataway, NJ USA, Aug. 30, 2006.

Butson, Christopher et al., "Predicting the Effects of Deep Brain Stimulation with Diffusion Tensor Based Electric Field Models"

(56) References Cited

OTHER PUBLICATIONS

Jan. 1, 2001, Medical Image Computing and Computer-Assisted Intervention-Mic CAI 2006 Lecture Notes in Computer Science; LNCS, Springer, Berlin, DE.
Butson, C. R., et al., “Deep brainstimulation interactive visualization system”, Society for Neuroscience vol. 898.7 (2005).
Hodaie, M., et al., “Chronic anterior thalamus stimulation for intractable epilepsy,” Epilepsia, 43(6) (Jun. 2002), pp. 603-608.
Hoekema, R., et al., “Multigrid solution of the potential field in modeling electrical nerve stimulation,” Comput Biomed Res., 31(5) (Oct. 1998), pp. 348-362.
Holsheimer, J., et al., “Identification of the target neuronal elements in electrical deep brain stimulation,” Eur J Neurosci., 12(12) (Dec. 2000), pp. 4573-4577.
Jezernik, S., et al., “Neural network classification of nerve activity recorded in a mixed nerve,” Neurol Res., 23(5) (Jul. 2001), pp. 429-434.
Jones, DK., et al., “Optimal strategies for measuring diffusion in anisotropic systems by magnetic resonance imaging,” Magn. Reson. Med., 42(3) (Sep. 1999), pp. 515-525.
Krack, P., et al., “Postoperative management of subthalamic nucleus stimulation for Parkinson’s disease,” Mov. Disord., vol. 17(suppl 3) (2002), pp. 188-197.
Le Bihan, D., et al., “Diffusion tensor imaging: concepts and applications,” J Magn Reson Imaging, 13(4) (Apr. 2001), pp. 534-546.
Lee, D. C., et al., “Extracellular electrical stimulation of central neurons: quantitative studies,” In: Handbook of neuroprosthetic methods, WE Finn and PG Lopresti (eds) CRC Press (2003), pp. 95-125.
Levy, AL., et al., “An Internet-connected, patient-specific, deformable brain atlas integrated into a surgical navigation system,” J Digit Imaging, 10(3 Suppl 1) (Aug. 1997), pp. 231-237.
Liu, Haiying, et al., “Intra-operative MR-guided DBS implantation for treating PD and ET,” Proceedings of SPIE vol. 4319, Department of Radiology & Neurosurgery, University of Minnesota, Minneapolis, MN 55455 (2001), pp. 272-276.
Mcintyre, C. C., et al., “Extracellular stimulation of central neurons: influence of stimulus waveform and frequency on neuronal output,” J. Neurophysiol., 88(4), (Oct. 2002), pp. 1592-1604.
Mcintyre, C. C., et al., “Microstimulation of spinal motoneurons: a model study,” Proceedings of the 19th Annual International Conference of the IEEE Engineering in Medicine and Biology society, vol. 5, (1997), pp. 2032-2034.
Mcintyre, Cameron C., et al., “Model-based Analysis of deep brain stimulation of the thalamus,” Proceedings of the Second joint EMBS/BM ES Conference, vol. 3, Annual Fall Meeting of the Biomedical Engineering Society (Cal. No. 02CH37392) IEEEPiscataway, NJ (2002), pp. 2047-2048.
Mcintyre, C. C., et al., “Model-based design of stimulus trains for selective microstimulation of targeted neuronal populations,” Proceedings of the 23rd Annual International Conference of the IEEE Engineering in Medicine and Biology Society, vol. 1 (2001), pp. 806-809.
Mcintyre, C. C., et al., Model-based design of stimulus waveforms for selective microstimulation in the central nervous system,, Proceedings of the First Joint [Engineering in Medicine and Biology, 1999. 21st Annual Conf. and the 1999 Annual FallMeeting of the Biomedical Engineering Soc] BM ES/EMBS Conference, vol. 1 (1999), p. 384.
Mcintyre, Cameron C., et al., “Modeling the excitability of mammalian nerve fibers: influence of aflerpotentials on the recovery cycle,” J Neurophysiol, 87(2) (Feb. 2002), pp. 995-1006.
Mcintyre, Cameron C., et al., “Selective microstimulation of central nervous system neurons,” Annals of biomedical engineering, 28(3) (Mar. 2000), pp. 219-233.
Mcintyre, C. C., et al., “Sensitivity analysis of a model of mammalian neural membrane,” Biol Cybern., 79(1) (Jul. 1998), pp. 29-37.
Mcintyre, Cameron C., et al., “Uncovering the mechanism(s) of action of deep brain stimulation: activation, inhibition, or both,” Clin Neurophysiol, 115(6) (Jun. 2004), pp. 1239-1248.
Mcintyre, Cameron C., et al., “Uncovering the mechanisms of deep brain stimulation for Parkinson’s disease through functional imaging, neural recording, and neural modeling,” Crit Rev Biomed Eng., 30(4-6) (2002), pp. 249-281.
Mouine et al. “Multi-Strategy and Multi-Algorithm Cochlear Prostheses”, Biomed. Sci. Instrument, 2000; 36:233-238.
Alo, K. M., et al., “New trends in neuromodulation for the management of neuropathic pain,” Neurosurgery, 50(4), (Apr. 2002), pp. 690-703, discussion pp. 703-704.
Ashby, P., et al., “Neurophysiological effects of stimulation through electrodes in the human subthalamic nucleus,” Brain, 122 (PI 10), (Oct. 1999), pp. 1919-1931.
Baker, K. B., et al., “Subthalamic nucleus deep brain stimulus evoked potentials: Physiological and therapeutic implications,” Movement Disorders, 17(5), (Sep./Ocl. 2002), pp. 969-983.
Bammer, R, et al., “Diffusion tensor imaging using single-shot SENSE-EPI”, Magn Reson Med., 48(1 ), (Jul. 2002), pp. 128-136.
Basser, P J., et al., “MR diffusion tensor spectroscopy and imaging,” Biophys J., 66(1 ), (Jan. 1994), pp. 259-267.
Basser, P J., et al., “New currents in electrical stimulation of excitable tissues,” Annu Rev Biomed Eng., 2, (2000), pp. 377-397.
Benabid, AL., et al., “Chronic electrical stimulation of the ventralis intermedius nucleus of the thalamus as a treatment of movement disorders,” J. Neurosurg., 84(2), (Feb. 1996), pp. 203-214.
Benabid, AL., et al., “Combined (Ihalamotoy and stimulation) stereotactic surgery of the VIM thalamic nucleus for bilateral Parkinson disease,” Appl Neurophysiol, vol. 50, (1987), pp. 344-346.
Benabid, A L., et al., “Long-term suppression of tremor by chronic stimulation of the ventral intermediate thalamic nucleus,” Lancet, 337 (8738), (Feb. 16, 1991 ), pp. 403-406.
Benoit M. Dawant et al: “The VU-DBS project: integrated and computer-assisted planning, intra-operative placement, and post-operative programming of deep-brain stimulators”, Proceedings of SPIE, vol. 6509, Mar. 6, 2007 (Mar. 6, 2007), 11 pages.
Christensen, Gary E., et al., “Volumetric transformation of brain anatomy,” IEEE Transactions on Medical Imaging, 16 (6), (Dec. 1997), pp. 864-877.
Cooper, S , et al., “Differential effects of thalamic stimulation parameters on tremor and paresthesias in essential tremor,” Movement Disorders, 17(Supp. 5), (2002), p. S193.
Coubes, P, et al., “Treatment of DYT1-generalised dystonia by stimulation of the internal globus pallidus,” Lancet, 355 (9222), (Jun. 24, 2000), pp. 2220-2221.
Pulliam CL, Heldman DA, Orcutt TH, Mera TO, Giuffrida JP, Vitek JL. Motion sensor strategies for automated optimization of deep brain stimulation in Parkinson’s disease. Parkinsonism Relat Disord. Apr. 2015; 21(4):378-82.
Dawant, B. M., et al., “Compuerized atlas-guided positioning of deep brain stimulators: a feasibility study,” Biomedical Image registration, Second International Workshop, WBIR 2003, Revised Papers (Lecture notes in Comput. Sci. vol. (2717), Springer-Verlag Berlin, Germany(2003), pp. 142-150.
Finnis, K. W., et al., “3-D functional atalas of subcortical structures for image guided stereotactic neurosurgery,” Neuroimage, vol. 9, No. 6, Iss. 2 (1999), p. S206.
Finnis, K. W., et al., “3D Functional Database of Subcorticol Structures for Surgical Guidance in Image Guided Stereotactic Neurosurgery,” Medical Image Computing and Computer-Assisted Intervention—MICCAI’99, Second International Conference. Cambridge, UK, Sep. 19-22, 1999, Proceedings (1999), pp. 758-767.
Finnis, K. W., et al., “A 3-Dimensional Database of Deep Brain Functional Anatomy, and Its Application to Image-Guided Neurosurgery,” Proceedings of the Third International Conference on Medical Image Computing and Computer-Assisted Intervention. Lecture Notes In Computer Science; vol. 1935 (2000), pp. 1-8.
Finnis, K. W., et al., “A functional database for guidance of surgical and therapeutic procedures in the deep brain,” Proceedings of the

(56) References Cited

OTHER PUBLICATIONS

22nd Annual International Conference of the IEEE Engineering in Medicine and Biology Society, vol. 3 (2000), pp. 1787-1789.
Finnis, K. W., et al., "Application of a Population Based Electrophysiological Database to the Planning and Guidance of Deep Brain Stereotactic Neurosurgery," Proceedings of the 5th International Conference on Medical Image Computing and Computer-Assisted Intervention-Part 11, Lecture Notes In Computer Science; vol. 2489 (2002), pp. 69-76.
Finnis, K. W., et al., "Subcortical physiology deformed into a patient-specific brain atlas for image-guided stereotaxy," Proceedings of SPIE—vol. 4681 Medical Imaging 2002: Visualization, Image-Guided Procedures, and Display (May 2002), pp. 184-195.
Finnis, Krik W., et al., "Three-Dimensional Database of Subcortical Electrophysiology for Image-Guided Stereotatic Functional Neurosurgery," IEEE Transactions on Medical Imaging, 22(1) (Jan. 2003), pp. 93-104.
Gabriels, L , et al., "Deep brain stimulation for treatment-refractory obsessive-compulsive disorder: psychopathological and neuropsychological outcome in three cases," Acta Psychiatr Scand., 107(4) (2003), pp. 275-282.
Gabriels, LA., et al., "Long-term electrical capsular stimulation in patients with obsessive-compulsive disorder," Neurosurgery, 52(6) (Jun. 2003), pp. 1263-1276.
Goodall, E. V., et al., "Modeling study of activation and propagation delays during stimulation of peripheral nerve fibers with a tripolar cuff electrode," IEEE Transactions on Rehabilitation Engineering, [see also IEEE Trans. on Neural Systems and Rehabilitation], 3(3) (Sep. 1995), pp. 272-282.
Goodall, E. V., et al., "Position-selective activation of peripheral nerve fibers with a cuff electrode," IEEE Transactions on Biomedical Engineering, 43(8) (Aug. 1996), pp. 851-856.
Goodall, E. V., "Simulation of activation and propagation delay during tripolar neural stimulation," Proceedings of the 15th Annual International Conference of the IEEE Engineering in Medicine and Biology Society (1993), pp. 1203-1204.
Grill, WM., "Modeling the effects of electric fields on nerve fibers: influence of tissue electrical properties," IEEE Transactions on Biomedical Engineering, 46(8) (1999), pp. 918-928.
Grill, W. M., et al., "Neural and connective tissue response to long-term implantation of multiple contact nerve cuff electrodes," J Biomed Mater Res., 50(2) (May 2000), pp. 215-226.
Grill, W. M., "Neural modeling in neuromuscular and rehabilitation research," Proceedings of the 23rd Annual International Conference of the IEEE Engineering in Medicine and Biology Society, vol. 4 (2001 ), pp. 4065-4068.
Grill, W. M., et al., "Non-invasive measurement of the input-output properties of peripheral nerve stimulating electrodes," Journal of Neuroscience Methods, 65(1) (Mar. 1996), pp. 43-50.
Grill, W. M., et al., "Quantification of recruitment properties of multiple contact cuff electrodes," IEEE Transactions on Rehabilitation Engineering, [see also IEEE Trans. on Neural Systems and Rehabilitation], 4(2) (Jun. 1996), pp. 49-62.
Grill, W. M., "Spatially selective activation of peripheral nerve for neuroprosthetic applications," Ph.D. Case Western Reserve University, (1995), pp. 245 pages.
Grill, W. M., "Stability of the input-output properties of chronically implanted multiple contact nerve cuff stimulating electrodes," IEEE Transactions on Rehabilitation Engineering [see also IEEE Trans. on Neural Systems and Rehabilitation] (1998), pp. 364-373.
Grill, W. M., et al., "Deep brain stimulation creates an informational lesion of the stimulated nucleus", Neuroreport. 1517t (May 19, 2004 ), 1137-40.
Grill, W. M., et al., "Temporal stability of nerve cuff electrode recruitment properties," IEEE 17th Annual Conference Engineering in Medicine and Biology Society, vol. 2 (1995), pp. 1089-1090.
Gross, RE., et al., "Advances in neurostimulation for movement disorders," Neurol Res., 22(3) (Apr. 2000), pp. 247-258.
Guridi et al., "The subthalamic nucleus, hemiballismus and Parkinson's disease: reappraisal of a neurological dogma," Brain, vol. 124, 2001, pp. 5-19.
Haberler, C, et al., "No tissue damage by chronic deep brain stimulation in Parkinson's disease," Ann Neurol., 48(3) (Sep. 2000), pp. 372-376.
Hamel, W, et al., "Deep brain stimulation of the subthalamic nucleus in Parkinson's disease: evaluation of active electrode contacts," J Neurol Neurosurg Psychiatry, 74(8) (Aug. 2003), pp. 1036-1046.
Hanekom, "Modelling encapsulation tissue around cochlear implant electrodes," Med. Biol. Eng. Comput. vol. 43 (2005), pp. 47-55.
Haueisen, J , et al., "The influence of brain tissue anisotropy on human EEG and MEG," Neuroimage, 15(1) (Jan. 2002), pp. 159-166.
D'Haese et al. Medical Image Computing and Computer-Assisted Intervention—MICCAI 2005 Lecture Notes in Computer Science, 2005, vol. 3750, 2005, 427-434.
Rohde et al. IEEE Transactions on Medical Imaging, vol. 22 No. 11, 2003 p. 1470-1479.
Dawant et al., Biomedical Image Registration. Lecture Notes in Computer Science, 2003, vol. 2717, 2003, 142-150.
Miocinovic et al., "Stereotactiv Neurosurgical Planning, Recording, and Visualization for Deep Brain Stimulation in Non-Human Primates", Journal of Neuroscience Methods, 162:32-41, Apr. 5, 2007, XP022021469.
Gemmar et al., "Advanced Methods for Target Navigation Using Microelectrode Recordings in Stereotactic Neurosurgery for Deep Brain Stimulation", 21st IEEE International Symposium on Computer-Based Medical Systems, Jun. 17, 2008, pp. 99-104, XP031284774.
Acar et al., "Safety Anterior Commissure-Posterior Commissure-Based Target Calculation of the Subthalamic Nucleus in Functional Stereotactic Procedures", Stereotactic Funct. Neurosura., 85:287-291, Aug. 2007.
Andrade-Souza, "Comparison of Three Methods of Targeting the Subthalamic Nucleus for Chronic Stimulation in Parkinson's Disease", Neurosurgery, 56:360-368, Apr. 2005.
Anheim et al., "Improvement in Parkinson Disease by Subthalamic Nucleus Stimulation Based on Electrode Placement", Arch Neural., 65:612-616, May 2008.
Butson et al., "Tissue and Electrode Capacitance Reduce Neural Activation Volumes During Deep Brain Stimulation", Clinical Neurophysiology, 116:2490-2500, Oct. 2005.
Butson et al., "Sources and Effects of Electrode Impedance During Deep Brain Stimulation", Clinical Neurophysiology, 117:44 7-454, Dec. 2005.
D'Haese et al., "Computer-Aided Placement of Deep Brain Stimulators: From Planning to Intraoperative Guidance", IEEE Transaction on Medical Imaging, 24:1469-1478, Nov. 2005.
Gross et al., "Electrophysiological Mapping for the Implantation of Deep Brain Stimulators for Parkinson's Disease and Tremor", Movement Disorders, 21 : S259-S283, Jun. 2006.
Halpern et al., "Brain Shift During Deep Brain Stimulation Surgery for Parkinson's Disease", Stereotact Funct. Neurosurg., 86:37-43, published online Sep. 2007.
Herzog et al., "Most Effective Stimulation Site in Subthalamic Deep Brain Stimulation for Parkinson's Disease", Movement Disorders, 19:1050-1099, published on line Mar. 2004.
Jeon et al., A Feasibility Study of Optical Coherence Tomography for Guiding Deep Brain Probes, Journal of Neuroscience Methods, 154:96-101, Jun. 2006.
Khan et al., "Assessment of Brain Shift Related to Deep Brain Stimulation Surgery", Sterreotact Funct. Neurosurg., 86:44-53, published online Sep. 2007.
Koop et al., "Improvement in a Quantitative Measure of Bradykinesia After Microelectrode Recording in Patients with Parkinson's Disease During Deep Brain Stimulation Surgery", Movement Disorders, 21 :673-678, published on line Jan. 2006.
Lemaire et al., "Brain Mapping in Stereotactic Surgery: A Brief Overview from the Probabilistic Targeting to the Patient-Based Anatomic Mapping", NeuroImage, 37:S109-S115, available online Jun. 2007.

(56) References Cited

OTHER PUBLICATIONS

Machado et al., "Deep Brain Stimulation for Parkinson's Disease: Surgical Technique and Perioperative Management", Movement Disorders, 21 : S247-S258, Jun. 2006.
Maks et al., "Deep Brain Stimulation Activation Volumes and Their Association with Neurophysiological Mapping and Therapeutic Outcomes", Downloaded from jnnp.bmj.com, pp. 1-21, published online Apr. 2008.
Moran et al., "Real-Time Refinment of Subthalamic Nucleous Targeting Using Bayesian Decision-Making on the Root Mean Square Measure", Movement Disorders, 21: 1425-1431, published online Jun. 2006.
Sakamoto et al., "Homogeneous Fluorescence Assays for RNA Diagnosis by Pyrene-Conjugated 2'-0-Methyloligoribonucleotides", Nucleosides, Nucleotides, and Nucleric Acids, 26:1659-1664, on line publication Oct. 2007.
Winkler et al., The First Evaluation of Brain Shift During Functional Neurosurgery by Deformation Field Analysis, J. Neural. Neurosurg. Psychiatry, 76:1161-1163, Aug. 2005.
Yelnik et al., "A Three-Dimensional, Histological and Deformable Atlas of the Human Basal J Ganglia. I. Atlas Construction Based on Immunohistochemical and MRI Data", NeuroImage, 34:618,-638, Jan. 2007.
Ward, H. E., et al., "Update on deep brain stimulation for neuropsychiatric disorders," Neurobiol Dis 38 (3) (2010), pp. 346-353.
Alberts et al. "Bilateral subthalamic stimulation impairs cognitive-motor performance in Parkinson's disease patients." Brain (2008), 131, 3348-3360, Abstract.
Grill, WM., et al., "Electrical properties of implant encapsulation tissue", Ann Biomed Eng. vol. 22. (1994),23-33.
An, et al., "Prefronlal cortical projections to longitudinal columns in the midbrain periaqueductal gray in macaque monkeys," J Comp Neural 401 (4) (1998), pp. 455-479.
Haslinger, B., et al., "Frequency-correlated decreases of motor cortex activity associated with subthalamic nucleus stimulation in Parkinson's disease.", Neuroimage 28(3). (Nov. 15, 2005), 598-606.
Carmichael, S. T., et al., "Connectional networks within the orbital and medial prefrontal cortex of macaque monkeys," J Comp Neural 371 (2) (1996), pp. 179-207.
Croxson, et al., "Quantitative investigation of connections of the prefrontal cortex in the human and macaque using probabilistic diffusion tractography," J Neurosci 25 (39) (2005), pp. 8854-8866.
Frankemolle, et al., "Reversing cognitive-motor impairments in Parkinson's disease patients using a computational modelling approach to deep brain stimulation programming," Brain 133 (2010), pp. 746-761.
Freedman, et al., "Subcortical projections of area 25 (subgenual cortex) of the macaque monkey," J Comp Neurol 421 (2) (2000), pp. 172-188.
Giacobbe, et al., "Treatment resistant depression as a failure of brain homeostatic mechanisms: implications for deep brain stimulation," Exp Neural 219 (1) (2009), pp. 44-52.
Goodman, et al., "Deep brain stimulation for intractable obsessive compulsive disorder: pilot study using a blinded, staggered-onset design," Biol Psychiatry 67 (6) (2010), pp. 535-542.
Greenberg, et al., "Deep brain stimulation of the ventral internal capsule/ventral striatum for obsessive-compulsive disorder: world-wide experience," Mol Psychiatry 15 (1) (2010), pp. 64-79.
Greenberg et al., "Three-year outcomes in deep brain stimulation for highly resistant obsessive-compulsive disorder," Neuropsychopharmacology 31 (11) (2006), pp. 2384-2393.
Gutman, et al., "A tractography analysis of two deep brain stimulation white matter targets for depression," Biol Psychiatry 65 (4) (2009), pp. 276-282.
Haber, et al., "Reward-related cortical inputs define a large striatal region in primates that interface with associative cortical connections, providing a substrate for incentive-based learning," J Neurosci 26 (32) (2006), pp. 8368-8376.
Haber, et al., "Cognitive and limbic circuits that are affected by deep brain stimulation," Front Biosci 14 (2009), pp. 1823-1834.
Hines, M. L., et al., "The NEURON simulation environment," Neural Comput., 9(6) (Aug. 15, 1997), pp. 1179-1209.
Hua, et al., "Tract probability maps in stereotaxic spaces: analyses of white matter anatomy and tract-specific quantification," Neuroimage 39 (1) (2008), pp. 336-347.
Johansen-Berg, et al., "Anatomical connectivity of the subgenual cingulate region targeted with deep brain stimulation for treatment-resistant depression," Cereb Cortex 18 (6) (2008), pp. 1374-1383.
Kopell, et al., "Deep brain stimulation for psychiatric disorders," J Clin Neurophysiol 21 (1) (2004), pp. 51-67.
Lozano, et al., "Subcallosal cingulate gyrus deep brain stimulation for treatment-resistant depression," Biol Psychiatry 64 (6) (2008), pp. 461-467.
Lujan, et al., "Tracking the mechanisms of deep brain stimulation for neuropsychiatric disorders," Front Biosci 13 (2008), pp. 5892-5904.
Lujan, J.L et al., "Automated 3-Dimensional Brain Atlas Fitting to Microelectrode Recordings from Deep Brain Stimulation Surgeries," Stereotact. Fune !. Neurosurg. 87(2009), pp. 229-240.
Machado. et al., "Functional topography of the ventral striatum and anterior limb of the internal capsule determined by electrical stimulation of awake patients," Clin Neurophysiol 120 (11) (2009), pp. 1941-1948.
Malone, et al., "Deep brain stimulation of the ventral capsule/ventral striatum for treatment-resistant depression," Biol Psychiatry 65 (4) (2009), pp. 267-275.
Mayberg, H. S., et al., "Deep brain stimulation for treatment-resistant depression," Neuron, 45(5) (Mar. 3, 2005), pp. 651-660.
Mayberg, H. S., et al., "Limbic-cortical dysregulation: a proposed model of depression," J Neuropsychiatry Clin Neurosci. 9 (3) (1997), pp. 471-481.
McIntyre, C. C., et al., "Network perspectives on the mechanisms of deep brain stimulation," Neurobiol Dis 38 (3) (2010), pp. 329-337.
Miocinovic, S., et al., "Experimental and theoretical characterization of the voltage distribution generated by deep brain stimulation," Exp Neurol 216 (i) (2009), pp. 166-176.
Nuttin, et al., "Electrical stimulation in anterior limbs of internal capsules in patients with obsessive-compulsive disorder," Lancet 354 (9189) (1999), p. 1526.
Saxena, et al., "Cerebral glucose metabolism in obsessive-compulsive hoarding," Am J Psychiatry. 161 (6) (2004), pp. 1038-1048.
Viola, et al., "Importance-driven focus of attention," IEEE Trans Vis Comput Graph 12 (5) (2006), pp. 933-940.
Wakana, S., et al., "Reproducibility of quantitative tractography methods applied to cerebral white matter," Neuroimage 36 (3) (2007), pp. 630-644.
Mayr et al., "Basic Design and Construction of the Vienna FES Implants: Existing Solutions and Prospects for New Generations of Implants", Medical Engineering & Physics, 2001; 23:53-60.
International Search Report and Written Opinion for PCT Application No. PCT/US2024/026048 mailed Jun. 20, 2024.
Mitra PP, Pesaran B. Analysis of dynamic brain imaging data. Biophys J. Feb. 1999;76(2):691-708. doi: 10.1016/S0006-3495(99)77236-X. PMID: 9929474; PMCID: PMC 1300074.
Hammer N, Glätzner J, Feja C, Kühne C, Meixensberger J, et al. (2015) Human Vagus Nerve Branching in the Cervical Region. PLOS One 10(2): e0118006. Published: Feb. 13, 2015. https://doi.org/10.1371/journal.pone.0118006.
Mcintyre, Cameron , et al., "Finite element analysis of the current-density and electric field generated by metal microelectrodes", Ann Biomed Eng . 29(3), (2001 ), 227-235.
Foster, K. R., et al., "Dielectric properties of tissues and biological materials: a critical review.", Grit Rev Biomed Ena. 17(1 ). {1989),25-104.
Limousin, P., et al., "Electrical stimulation of the subthalamic nucleus in advanced Parkinson's disease", N Engl J Med . . . 339(16), (Oct. 15, 1998), 1105-11.

(56) References Cited

OTHER PUBLICATIONS

Kitagawa, M., et al., "Two-year follow-up of chronic stimulation of the posterior subthalamic white matter for tremor-dominant Parkinson's disease.", Neurosurgery. 56(2). (Feb. 2005),281-9.
Johnson, M. D., et al., "Repeated voltage biasing improves unit recordings by reducing resistive tissue impedances", IEEE Transactions on Neural Systems and Rehabilitation Engineering, [see also IEEE Trans. on Rehabilitation Engineering (2005), 160-165.
Holsheimer, J. , et al., "Chronaxie calculated from current-duration and voltage-duration data", J Neurosci Methods. 97(1). (Apr. 1, 2000),45-50.
Hardman, C. D., et al., "Comparison of the basal ganglia in rats, marmosets, macaques, baboons, and humans: volume and neuronal number for the output, internal relay, and striatal modulating nuclei", J Comp Neurol., 445(3). (Apr. 8, 2002),238-55.
Hashimoto, T. , et al., "Stimulation of the subthalamic nucleus changes the firing pattern of pallidal neurons", J Neurosci. 23(5). (Mar. 1, 2003), 1916-23.
Hershey, T., et al., "Cortical and subcortical blood flow effects of subthalamic nucleus stimulation in PD.", Neurology 61(6). (Sep. 23, 2003), 816-21.
Hemm, S. , et al., "Evolution of Brain Impedance in Dystonic Patients Treated by GPi Electrical Stimulation", Neuromodulation 7(2) (Apr. 2004),67-75.
Hemm, S., et al., "Deep brain stimulation in movement disorders: stereotactic coregistration of two-dimensional electrical field modeling and magnetic resonance imaging.", J Neurosurg. 103(6): (Dec. 2005), 949-55.
C.R. Butson, J. Hall, J. Henderson, C. McIntyre. Patient-Specific Models of Deep Brain Stimulation: 3D Visualization of Anatomy, Electrode and Volume of Activation as a Function of Stimulation Parameters Program No. 1011.11. 2004 Abstract. Washington, DC: Society for Neuroscience, 2004. Online.
Trost M, Su S, Su P, Yen RF, Tseng HM, Barnes A, Ma Y, Eidelberg D. Network modulation by the subthalamic nucleus in the treatment of Parkinson's disease. Neuroimage. May 15, 2006;31(1):301-7. doi: 10.1016/j.neuroimage.2005.12.024. Epub Feb. 8, 2006.
Mcintyre, Cameron C., et al., "Electric Field and Stimulating Influence generated by Deep Brain Stimulation of the Subthalamaic Nucleus," Clinical Neurophysiology, 115(3) (Mar. 2004), pp. 589-595.
Mcintyre, Cameron C., et al., "Electric field generated by deep brain stimulation of the subthalamic nucleus," Biomedical Engineering Society Annual Meeting, Nashville TN (Oct. 2003), 16 pages.
Mcintyre, Cameron C., et al., "Excitation of central nervous system neurons by nonuniform electric fields," Biophys. J., 76(2) (1999), pp. 878-888.
McNeal, DR., et al., "Analysis of a model for excitation of myelinated nerve," IEEE Trans Biomed Eng., vol. 23 (1976), pp. 329-337.
McNaughtan et al., "Electrochemical Issues in Impedance Tomography", 1st World Congress on Industrial Process Tomography, Buxton, Greater Manchester, Apr. 14-17, 1999.
Miocinovic, S., et al., "Computational analysis of subthalamic nucleus and lenticular fasciculus activation during therapeutic deep brain stimulation," J Neurophysiol., 96(3) (Sep. 2006), pp. 1569-1580.
Miranda, P. C., et al., "The distribution of currents inducedin the brain by Magnetic Stimulation: a finite element analysis incorporating OT-MRI-derived conductivity data," Proc. Intl. Soc. Mag. Reson. Med. 9 (2001 ), p. 1540.
Miranda, P. C., et al., "The Electric Field Induced in the Brain by Magnetic Stimulation: A 3-D Finite-Element Analysis of the Effect of Tissue Heterogeneity and Anisotropy," IEEE Transactions on Biomedical Engineering, 50(9) (Sep. 2003), pp. 1074-1085.
Moffitt, MA., et al., "Prediction of myelinated nerve fiber stimulation thresholds: limitations of linear models," IEEE Transactions on Biomedical Engineering, 51 (2) (2003), pp. 229-236.
Moro, E, et al., "The impact on Parkinson's disease of electrical parameter settings in STN stimulation," Neurology, 59 (5) (Sep. 10, 2002), pp. 706-713.
Nowak, LG., et al., "Axons, but not cell bodies, are activated by electrical stimulation in cortical gray matter. I. Evidence from chronaxie measurements," Exp. Brain Res., 118(4) (Feb. 1998), pp. 477-488.
Nowak, LG., et al., "Axons, but not cell bodies, are activated by electrical stimulation in cortical gray matter. II. Evidence from selective inactivation of cell bodies and axon initial segments," Exp. Brain Res., 118(4) (Feb. 1998), pp. 489-500.
O'Suilleabhain, PE., et al., "Tremor response to polarity, voltage, pulsewidth and frequency of thalamic stimulation," Neurology, 60(5) (Mar. 11, 2003), pp. 786-790.
Pierpaoli, C., et al., "Toward a quantitative assessment of diffusion anisotropy," Magn Reson Med., 36(6) (Dec. 1996), pp. 893-906.
Plonsey, R., et al., "Considerations of quasi-stationarity in electrophysiological systems," Bull Math Biophys., 29(4) (Dec. 1967), pp. 657-664.
Ranck, J B., "Specific impedance of rabbit cerebral cortex," Exp. Neurol., vol. 7 (Feb. 1963), pp. 144-152.
Ranck, J B., et al., "The Specific impedance of the dorsal columns of the cat: an anisotropic medium," Exp. Neurol., 11 (Apr. 1965), pp. 451-463.
Ranck, J B., "Which elements are excited in electrical stimulation of mammalian central nervous system: a review," Brain Res., 98(3) (Nov. 21, 1975), pp. 417-440.
Rattay, F., et al., "A model of the electrically excited human cochlear neuron. I. Contribution of neural substructures to the generation and propagation of spikes," Hear Res., 153(1-2) (Mar. 2001), pp. 43-63.
Rattay, F., "A model of the electrically excited human cochlear neuron. II. Influence of the three-dimensional cochlear structure on neural excitability," Hear Res., 153(1-2) (Mar. 2001), pp. 64-79.
Rattay, F., "Arrival at Functional Electrostimulation by modelling of fiber excitation," Proceedings of the Ninth annual Conference of the IEEE Engineering in Medicine and Biology Society (1987), pp. 1459-1460.
Rattay, F., "The influence of intrinsic noise can preserve the temporal fine structure of speech signals in models of electrically stimulated human cochlear neurones," Journal of Physiology, Scientific Meeting of the Physiological Society, London, England, UK Apr. 19-21, 1999 (Jul. 1999), p. 170P.
Rizzone, M., et al., "Deep brain stimulation of the subthalamic nucleus in Parkinson's disease: effects of variation in stimulation parameters," J. Neurol. Neurosurg. Psychiatry., 71(2) (Aug. 2001), pp. 215-219.
Saint-Cyr, J. A., et al., "Localization of clinically effective stimulating electrodes in the human subthalamic nucleus on magnetic resonance imaging," J. Neurosurg., 87(5) (Nov. 2002), pp. 1152-1166.
Sances, A., et al., "In Electroanesthesia: Biomedical and Biophysical Studies," A Sances and SJ Larson, Eds., Academic Press, NY (1975), pp. 114-124.
SI. Jean, P., et al., "Automated atlas integration and interactive three-dimensional visualization tools for planning and guidance in functional neurosurgery," IEEE Transactions on Medical Imaging, 17(5) (1998), pp. 672-680.
Starr, P.A., et al., "Implantation of deep brain stimulators into the subthalamic nucleus: technical approach and magnetic resonance imaging-verified lead locations," J. Neurosurg., 97(2) (Aug. 2002), pp. 370-387.
Sterio, D., et al., "Neurophysiological refinement of subthalamic nucleus targeting," Neurosurgery, 50(1) (Jan. 2002), pp. 58-69.
Struijk, J. J., et al., "Excitation of dorsal root fibers in spinal cord stimulation: a theoretical study," IEEE Transactions on Biomedical Engineering, 40(7) (Jul. 1993), pp. 632-639.
Struijk, J J., et al., "Recruitment of dorsal column fibers in spinal cord stimulation: influence of collateral branching," IEEE Transactions on Biomedical Engineering, 39(9) (Sep. 1992), pp. 903-912.
Tamma, F., et al., "Anatomo-clinical correlation of intraoperative stimulation-induced side-effects during HF-DBS of the subthalamic nucleus," Neurol Sci., vol. 23 (Suppl 2) (2002), pp. 109-110.
Tarler, M., et al., "Comparison between monopolar and tripolar configurations in chronically implanted nerve cuff electrodes,"

(56) References Cited

OTHER PUBLICATIONS

IEEE 17th Annual Conference Engineering in Medicine and Biology Society, vol. 2 (1995), pp. 1093-1109.
Testerman, Roy L., "Coritical response to callosal stimulation: A model for determining safe and efficient stimulus parameters," Annals of Biomedical Engineering, 6(4) (1978), pp. 438-452.
Tuch, D.S., et al., "Conductivity mapping of biological tissue using diffusion MRI," Ann NY Acad Sci., 888 (Oct. 30, 1999), pp. 314-316.
Tuch, D.S., et al., "Conductivity tensor mapping of the human brain using diffusion tensor MRI," Proc Nall Acad Sci USA, 98(20) (Sep. 25, 2001), pp. 11697-11701.
Veraart, C., et al., "Selective control of muscle activation with a multipolar nerve cuff electrode," IEEE Transactions on Biomedical Engineering, 40(7) (Jul. 1993), pp. 640-653.
Vercueil, L., et al., "Deep brain stimulation in the treatment of severe dystonia," J. Neurol., 248(8) (Aug. 2001 ), pp. 695-700.
Vilalte, "Circuit Design of the Power-on-Reset," Apr. 2000, pp. 1-25.
Vitek, J. L., "Mechanisms of deep brain stimulation: excitation or inhibition," Mov. Disord., vol. 17 (Suppl. 3) (2002), pp. 69-72.
Voges, J., et al., "Bilateral high-frequency stimulation in the subthalamic nucleus for the treatment of Parkinson disease: correlation of therapeutic effect with anatomical electrode position," J. Neurosurg., 96(2) (Feb. 2002), pp. 269-279.
Wakana, S., et al., "Fiber tract-based atlas of human white matter anatomy," Radiology, 230(1) (Jan. 2004), pp. 77-87.
Alexander, DC., et al., "Spatial transformations of diffusion tensor magnetic resonance images," IEEE Transactions on Medical Imaging, 20 (11), (2001), pp. 1131-1139.
Wu, Y. R., et al., "Does Stimulation of the GPi control dyskinesia by activating inhibitory axons?," Mov. Disord., vol. 16 (2001), pp. 208-216.
Yelnik, J., et al., "Localization of stimulating electrodes in patients with Parkinson disease by using a three-dimensional atlas-magnetic resonance imaging coregistration method," J Neurosurg., 99(1) (Jul. 2003), pp. 89-99.
Manni, John, et al., "Globus pallidus internus deep brain stimulation for dystonic conditions: a prospective audit," Mov. Disord., vol. 18 (2003), pp. 436-442.
Zonenshayn, M., et al., "Comparison of anatomic and neurophysiological methods for subthalamic nucleus targeting," Neurosurgery, 47(2) (Aug. 2000), pp. 282-294.
Voghell et al., "Programmable Current Source Dedicated to Implantable Microstimulators" ICM '98 Proceedings of the Tenth International Conference, pp. 67-70.
Butson, Christopher R., et al., "Patient-specific analysis of the volume of tissue activated during deep brain stimulation", NeuroImage. vol. 34. (2007),661-670.
Adler, DE., et al., "The tentorial notch: anatomical variation, morphometric analysis, and classification in 100 human autopsy cases," J. Neurosurg., 96(6), (Jun. 2002), pp. 1103-1112.
Jones et al., "An Advanced Demultiplexing System for Physiological Stimulation", IEEE Transactions on Biomedical Engineering, vol. 44 No. 12 Dec. 1997, pp. 1210-1220.
Nowinski, W. L., et al., "Statistical analysis of 168 bilateral subthalamic nucleus implantations by means of the probabilistic functional atlas.", Neurosurgery 57(4 Suppl) (Oct. 2005),319-30.
Obeso, J. A., et al., "Deep-brain stimulation of the subthalamic nucleus or the pars interna of the globus pallidus in Parkinson's disease.", N Engl J Med., 345{131. The Deep-Brain Stimulation for Parkinson's Disease Study Group, (Sep. 27, 2001 ), 956-63.
Butson et al.. "Current Steering to control the volume of tissue activated during deep brain stimulation," vol. 1, No. 1, Dec 3, 2007, pp. 7-15.
Patrick, S. K., et al., "Quantification of the UPDRS rigidity scale", IEEE Transactions on Neural Systems and Rehabilitation Engineering, [see also IEEE Trans. on Rehabilitation Engineering 9(1). (2001), 31-41.
Phillips, M. D., et al., "Parkinson disease: pattern of functional MR imaging activation during deep brain stimulation of subthalamic nucleus—initial experience", Radiology 239(1). (Apr. 2006),209-16.
Ericsson, A. et al., "Construction of a patient-specific atlas of the brain: Application to normal aging," Biomedical Imaging: From Nano to Macro, ISBI 2008, 5th IEEE International Symposium, May 14, 2008, pp. 480-483.
Kaikai Shen et al., "Atlas selection strategy using least angle regression in multi-atlas segmentation propagation," Biomedical Imaging: From Nano to Macro, 2011, 8th IEEE International Symposium, ISBI 2011, Mar. 30, 2011, pp. 1746-1749.
Liliane Ramus et al., "Assessing selection methods in the cotnext of multi-atlas based segmentation," Biomedical Imaging: From Nano to Macro, 2010, IEEE International Symposium, Apr. 14, 2010, pp. 1321-1324.
Olivier Commowick et al., "Using Frankenstein's Creature Paradigm to Build a Patient Specific Atlas," Sep. 20, 2009, Medical Image Computing and Computer-Assisted Intervention, pp. 993-1000.
Lotjonen J.M.P. et al., "Fast and robust multi-atlas segmentation of brain magnetic resonance images," NeuroImage, Academic Press, vol. 49, No. 3, Feb. 1, 2010, pp. 2352-2365.
Mcintyre, C. C., et al., "How does deep brain stimulation work? Present understanding and future questions.", J Clin Neurophysiol. 21 (1 ). (Jan.-Feb. 2004 ), 40-50.
Sanchez Castro et al., "A cross validation study of deep brain stimulation targeting: From experts to Atlas-Based, Segmentation-Based and Automatic Registration Algorithms," IEEE Transactions on Medical Imaging, vol. 25, No. 11, Nov. 1, 2006, pp. 1440-1450.
Plaha, P., et al., "Stimulation of the caudal zona incerta is superior to stimulation of the subthalamic nucleus in improving contralateral parkinsonism.", Brain 129{Pt 7) (Jul. 2006), 1732-4 7.
Rattay, F, "Analysis of models for external stimulation of axons", IEEE Trans. Biomed. Eng. vol. 33 (1986), 974-977.
Rattay, F., "Analysis of the electrical excitation of CNS neurons", IEEE Transactions on Biomedical Engineering 45 (6). (Jun. 1998),766-772.
Rose, T. L., et al., "Electrical stimulation with Pt electrodes. VIII. Electrochemically safe charge injection limits with 0.2 ms pulses [neuronal application]", IEEE Transactions on Biomedical Engineering, 37(11 }, (Nov. 1990), 1118-1120.
Rubinstein, J. T., et al., "Signal coding in cochlear implants: exploiting stochastic effects of electrical stimulation", Ann Otol Rhinol Laryngol Suppl .. 191, (Sep. 2003), 14-9.
Schwan, H.P., et al., "The conductivity of living tissues.", Ann NY Acad Sci., 65(6). (AUQ., 1957), 1007-13.
Taylor, R. S., et al., "Spinal cord stimulation for chronic back and leg pain and failed back surgery syndrome: a systematic review and analysis of prognostic factors", Spine 30(1 ). (Jan. 1, 2005), 152-60.
Siegel, Ralph M. et al., "Spatiotemporal dynamics of the functional architecture for gain fields in inferior parietal lobule of behaving monkey," Cerebral Cortex, New York, NY, vol. 17, No. 2, Feb. 2007, pp. 378-390.
Klein, A. et al., "Evaluation of 14 nonlinear deformation algorithms applied to human brain MRI registration," NeuroImage, Academic Press, Orlando, FL, vol. 46, No. 3, Jul. 2009, pp. 786-802.
Geddes, L. A., et al., "The specific resistance of biological material—a compendium of data for the biomedical engineer and physiologist.", Med Biol Ena. 5(3). (May 1967),271-93.
Gimsa, J., et al., "Choosing electrodes for deep brain stimulation experiments-electrochemical considerations.", J Neurosci Methods, 142(2), (Mar. 30, 2005),251-65.
Vidailhet, M. , et al., "Bilateral deep-brain stimulation of the globus pallidus in primary generalized dystonia", N Engl J Med. 352(5) (Feb. 3, 2005),459-67.
Izad, Oliver, "Computationally Efficient Method in Predicating Axonal Excitation," Dissertation for Master Degree, Department of Biomedical Engineering, Case Western Reserve University, May 2009.
Jaccard, Paul, "Elude comparative de la distribution florale dans une portion odes Aples et des Jura," Bulletin de la Societe Vaudoise des Sciences Naturelles (1901), 37:547-579.

(56) References Cited

OTHER PUBLICATIONS

Dice, Lee R., "Measures of the Amount of Ecologic Association Between Species," Ecology 26(3) (1945): 297-302. doi: 10.2307/1932409, http://jstor.org/stable/1932409.
Rand, WM., "Objective criteria for the evaluation of clustering methods," Journal of the American Statistical Association (American Statistical Association) 66 (336) (1971 ): 846-850, doi:10.2307/2284239, http://jstor.org/stable/2284239.
Hubert, Lawrence et al., "Comparing partitions," Journal of Classification 2(1) (1985): 193-218, doi:10.1007/ BF01908075.
Cover, T.M. et al., "Elements of information theory," (1991) John Wiley & Sons, New York, NY.
Meila, Marina, "Comparing Clusterings by the Variation of Information," Learning Theory and Kernel Machines (2003): 173-187.
Viola, P., et al., "Alignment by maximization of mutual information", International Journal of Com outer Vision 24(2). ( 1997), 137-154.
Butson et al. "StimExplorer: Deep Brain Stimulation Parameter Selection Software System," Acta Neurochirugica, Jan. 1, 2007, vol. 97, No. 2, pp. 569-574.
Butson et al. "Role of Electrode Design on the Volume of Tissue Activated During Deep Brain Stimulation," Journal of Neural Engineering, Mar. 1, 2006, vol. 3, No. 1, pp. 1-8.
Volkmann et al., Indroduction to the Programming of Deep Brain Stimulators, Movement Disorders, vol. 17, Suppl. 3, pp. S181-S187 (2002).
Miocinovic et al. "Cicerone: Stereotactic Neurophysiological Recording and Deep Brain Stimulation Electrode Placement Software System," Acta Neurochirurgica Suppl., Jan. 1, 2007, vol. 97, No. 2, pp. 561-567.
Schmidt et al. "Sketching and Composing Widgets for 3D Manipulation," Eurographics, Apr. 2008, vol. 27, No. 2, pp. 301-310.
Volkmann, J. , et al., "Basic algorithms for the programming of deep brain stimulation in Parkinson's disease", Mov Disord., 21 Suppl 14. (Jun. 2006), S284-9.
Walter, B. L., et al., "Surgical treatment for Parkinson's disease", Lancet Neural. 3(12). (Dec. 2004), 719-28.
Wei, X. F., et al., "Current density distributions, field distributions and impedance analysis of segmented deep brain stimulation electrodes", J Neural Eng .. 2(4). (Dec. 2005), 139-47.
Zonenshayn, M. , et al., "Location of the active contact within the subthalamic nucleus (STN) in the treatment of idiopathic Parkinson's disease.", Surg Neurol., 62(3) (Sep. 2004),216-25.
Da Silva et al.(A primer on diffusion tensor imaging of anatomical substructures. Neurosurg Focus 15(1): p. 1-4, Article 4, 2003.).
Micheli-Tzanakou, E., et al., "Computational Intelligence for target assesment in Parkinson's disease", Proceedings of SPIE vol. 4479. Applications and Science of Neural Networks, Fuzzy Systems, and Evolutionary Computation IV,(2001),54-69.
Grill, W. M., "Stimulus waveforms for selective neural stimulation", IEEE Engineering in Medicine and Biology Magazine, 14(4}, (Jul.-Aug. 1995), 375-385.
Miocinovic, S., et al., "Sensitivity of temporal excitation properties to the neuronal element activated by extracellular stimulation", J Neurosci Methods. 132(1). (Jan. 15, 2004), 91-9.
Hunka, K. et al., Nursing Time to Program and Assess Deep Brain Stimulators in Movement Disorder Patients, J. Neursci Nurs., 37: 204-10 (Aug. 2005).
Moss, J. , et al., "Electron microscopy of tissue adherent to explanted electrodes in dystonia and Parkinson's disease", Brain, 127{Pt 12). (Dec. 2004 ),2755-63.
Montgomery, E. B., et al., "Mechanisms of deep brain stimulation and future technical developments.", Neurol Res. 22(3). (Apr. 2000),259-66.
Merrill, D. R., et al., "Electrical stimulation of excitable tissue: design of efficacious and safe protocols", J Neurosci Methods. 141(2), (Feb. 15, 2005), 171-98.
Fisekovic et al., "New Controller for Functional Electrical Stimulation Systems", Med. Eng. Phys. 2001; 23:391-399.

* cited by examiner

SYSTEMS AND METHODS FOR MODIFYING STIMULATION IN RESPONSE TO A CHANGE IN A SYMPTOM, THERAPEUTIC EFFECT, OR SIDE EFFECT

CROSS-REFERENCE TO RELATED APPLICATIONS

This application claims the benefit under 35 U.S.C. § 119(e) of U.S. Provisional Patent Application Ser. No. 63/462,905, filed Apr. 28, 2023, which is incorporated herein by reference.

FIELD

The present disclosure is directed to methods and systems for stimulation of a patient. The present disclosure is also directed to methods and systems for modifying stimulation in response to a change in a symptom, therapeutic effect, or side effect.

BACKGROUND

Implantable electrical stimulation systems have proven therapeutic in a variety of diseases and disorders. For example, deep brain stimulation systems have been used as a therapeutic modality for the treatment of Parkinson's disease, essential tremor, and the like.

Stimulators have been developed to provide therapy for a variety of treatments. A stimulator can include an implantable pulse generator (IPG), one or more leads, and an array of stimulator electrodes on each lead. The stimulator electrodes are in contact with or near the nerves, muscles, or other tissue to be stimulated. The pulse generator in the IPG generates electrical pulses that are delivered by the electrodes to body tissue.

Implantable medical devices (IMDs), including IPGs, typically have the capability to communicate data with an external device, such as a clinician programmer or a remote control, via a radio-frequency telemetry link or other wireless communication method. The clinician programmer can program the operating parameters of the implanted medical device. The remote control can switch programs. Modern implantable devices also include the capability for bidirectional communication so that information can be transmitted to the clinician programmer or remote control from the implanted device.

BRIEF SUMMARY

One aspect is a method for adapting stimulation by a stimulation system to a change in a symptom, therapeutic effect, or side effect, the stimulation system including a stimulation device implanted in a patient. The method includes detecting a change in a symptom of a disease or disorder or in a therapeutic effect or a side effect of stimulation by the stimulation system; in response to the detecting, determining, by the stimulation system, a modification of one or more stimulation parameter values to adapt to the change in the symptom, the therapeutic effect, or the side effect; and at least one of the following: 1) suggesting to the patient or to a clinician adoption of the modification and, upon receiving affirmation from the patient or the clinician, stimulating the patient according to the modification of the one or more stimulation parameter values, or 2) automatically stimulating the patient according to the modification of the one or more stimulation parameter values.

Another aspect is a stimulation system that includes a memory having instructions stored thereon and a processor configured for executing the instructions to perform actions including detecting a change in a symptom of a disease or disorder or in a therapeutic effect or a side effect of stimulation by the stimulation system; in response to the detecting, determining, by the stimulation system, a modification of one or more stimulation parameter values to adapt to the change in the symptom, the therapeutic effect, or the side effect; and at least one of the following: 1) suggesting to a patient or to a clinician adoption of the modification and, upon receiving affirmation from the patient or the clinician, stimulating the patient according to the modification of the one or more stimulation parameter values, or 2) automatically directing stimulation of the patient according to the modification of the one or more stimulation parameter values.

Yet another aspect is a non-transient computer readable medium having stored thereon instructions for performing actions for adapting stimulation by a stimulation system to a change in a symptom, therapeutic effect, or side effect, the actions including detecting a change in a symptom of a disease or disorder or in a therapeutic effect or a side effect of stimulation by the stimulation system; in response to the detecting, determining, by the stimulation system, a modification of one or more stimulation parameter values to adapt to the change in the symptom, the therapeutic effect, or the side effect; and at least one of the following: 1) suggesting to a patient or to a clinician adoption of the modification and, upon receiving affirmation from the patient or the clinician, stimulating the patient according to the modification of the one or more stimulation parameter values, or 2) automatically directing stimulation of the patient according to the modification of the one or more stimulation parameter values.

In at least some aspects, the symptom or side effect is dyskinesia. In at least some aspects, the symptom or side effect is freezing of gait.

In at least some aspects, detecting the change includes detecting the change using a sensor disposed on or within the patient. In at least some aspects, detecting the change includes detecting the change from information provided to the stimulation system by the patient, a caregiver, or a clinician.

In at least some aspects, the method or actions further include logging the change into a memory of the stimulation system. In at least some aspects, the logging the change further includes logging a time of the change into the memory of the stimulation system. In at least some aspects, the method or the actions further include logging whether the modification of the one or more stimulation parameter values is successful in addressing the change.

In at least some aspects, the method or the actions further include, in response to the detecting, notifying at least one of the patient or the clinician of the change. In at least some aspects, detecting the change includes detecting the change when the change includes an increase or decrease by a predetermined magnitude of at least one measured indicator. In at least some aspects, detecting the change includes detecting the change when the change includes an increase or decrease for at least a predetermined period of time of at least one measured indicator. In at least some aspects, the method or the actions further include determining whether the modification of the one or more stimulation parameter values increases or decreases the symptom or side effect.

Another aspect is a method for modifying stimulation by a stimulation system including a stimulation device implanted in a patient in response to an identified trend. The method includes identifying, by the stimulation system and over a period of time, a trend of adjustment of the stimulation in response to a trigger event; defining a schedule for the adjustment of the stimulation based on the identified trend; and automatically, or with affirmation by the patient or clinician, directing the adjustment of the stimulation according to the schedule.

A further aspect is a stimulation system that includes a memory having instructions stored thereon and a processor configured for executing the instructions to perform actions including identifying, by the stimulation system and over a period of time, a trend of adjustment of the stimulation in response to a trigger event; defining a schedule for the adjustment of the stimulation based on the identified trend; and automatically, or with affirmation by the patient or clinician, directing the adjustment of the stimulation according to the schedule.

Yet another aspect is a non-transient computer readable medium having stored thereon instructions for performing actions for modifying stimulation by a stimulation system, the actions including identifying, by the stimulation system and over a period of time, a trend of adjustment of the stimulation in response to a trigger event; defining a schedule for the adjustment of the stimulation based on the identified trend; and automatically, or with affirmation by the patient or clinician, directing the adjustment of the stimulation according to the schedule.

In at least some aspects, the trend includes the adjustment of the stimulation at a particular time of day. In at least some aspects, the trend includes the adjustment of the stimulation in response to administration of medication. In at least some aspects, the trend includes the adjustment of the stimulation in response to a determination that the patient is engaging in a specified activity.

In at least some aspects, the trend includes the adjustment of the stimulation in response to a change in a symptom of a disease or disorder or in a therapeutic effect or a side effect of stimulation by the stimulation system. In at least some aspects, the method or the actions further include detecting the change when the change includes an increase or decrease for at least a predetermined period of time of at least one measured indicator. In at least some aspects, the method or the actions further include detecting the change when the change includes an increase or decrease by a predetermined magnitude of at least one measured indicator. In at least some aspects, the method or the actions further include detecting the change using a sensor disposed on or within the patient.

BRIEF DESCRIPTION OF THE DRAWINGS

Non-limiting and non-exhaustive embodiments of the present invention are described with reference to the following drawings. In the drawings, like reference numerals refer to like parts throughout the various figures unless otherwise specified.

For a better understanding of the present invention, reference will be made to the following Detailed Description, which is to be read in association with the accompanying drawings, wherein.

DETAILED DESCRIPTION

The present disclosure is directed to methods and systems for stimulation of a patient. The present disclosure is also directed to methods and systems for modifying stimulation in response to a change in a symptom, therapeutic effect, or side effect.

Implantable electrical stimulation systems and devices are used herein to exemplify the inventions, but it will be understood that these inventions can be utilized with other stimulation or modulation systems and devices, such as optical or electrical/optical stimulation or modulation systems. Examples of implantable electrical stimulation systems include, but are not limited to, a least one lead with one or more electrodes disposed along a distal end of the lead and one or more terminals disposed along the one or more proximal ends of the lead. Examples of electrical stimulation systems with leads are found in, for example, U.S. Pat. Nos. 6,181,969; 6,295,944; 6,391,985; 6,516,227; 6,609,029; 6,609,032; 6,741,892; 7,244,150; 7,450,997; 7,672,734; 7,761,165; 7,783,359; 7,792,590; 7,809,446; 7,949,395; 7,974,706; 8,831,742; 8,688,235; 8,175,710; 8,224,450; 8,271,094; 8,295,944; 8,364,278; and 8,391,985; U.S. Patent Application Publications Nos. 2007/0150036; 2009/0187222; 2009/0276021; 2010/0076535; 2010/0268298; 2011/0004267; 2011/0078900; 2011/0130817; 2011/0130818; 2011/0238129; 2011/0313500; 2012/0016378; 2012/0046710; 2012/0071949; 2012/0165911; 2012/0197375; 2012/0203316; 2012/0203320; 2012/0203321; 2012/0316615; 2013/0105071; 2011/0005069; 2010/0268298; 2011/0130817; 2011/0130818; 2011/0078900; 2011/0238129; 2011/0313500; 2012/0016378; 2012/0046710; 2012/0165911; 2012/0197375; 2012/0203316; 2012/0203320; and 2012/0203321, all of which are incorporated by reference in their entireties. Examples of optical stimulation or modulation systems or electrical/optical stimulation systems, which include one or more optical emitters in addition to, or as an alternative to, electrodes, are found in U.S. Pat. Nos. 9,415,154; 10,335,607; 10,625,072; and 10,814,140 and U.S. Patent Application Publications Nos. 2013/0317572; 2013/0317573; 2017/0259078; 2017/0225007; 2018/0110971; 2018/0369606; 2018/0369607; 2019/0209849; 2019/0209834; 2020/0094047; 2020/

0155584; 2020/0376262; 2021/0008388; 2021/0008389; 2021/0016111; and 2022/0072329, all of which are incorporated by reference in their entireties.

Figure 1:
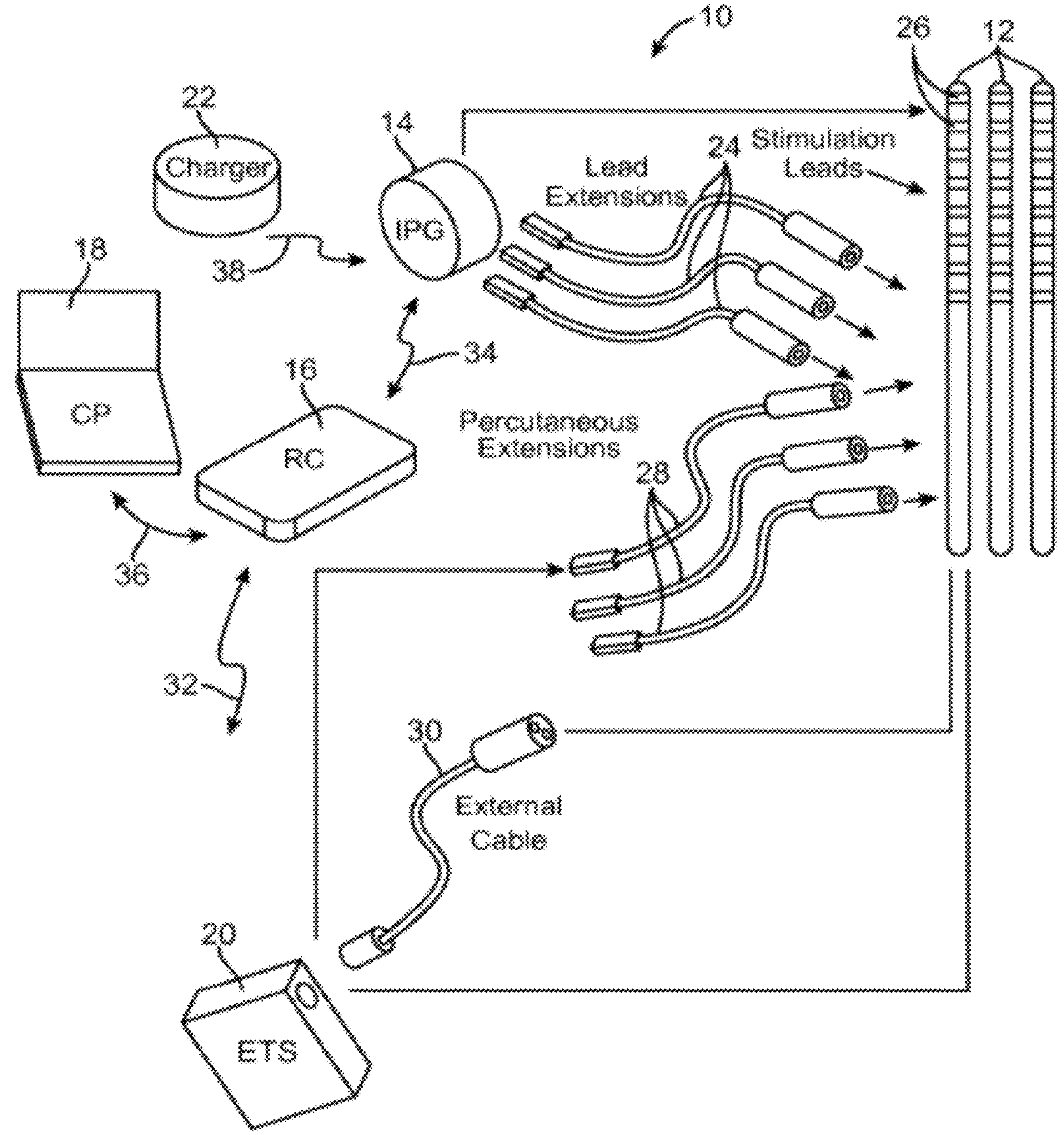
FIG. 1 is a schematic view of one embodiment of an electrical stimulation system that includes one or more leads that can be coupled to an IPG.

Turning to FIG. 1, one embodiment of an electrical stimulation system 10 includes one or more stimulation leads 12 and an implantable pulse generator (IPG) 14. The stimulation system 10 can also include one or more of an external remote control (RC) 16, a clinician's programmer (CP) 18, an external trial stimulator (ETS) 20, or an external charger 22. The IPG and ETS are examples of control modules for the electrical stimulation system.

The IPG 14 is physically connected, optionally via one or more lead extensions 24, to the stimulation lead(s) 12. Each lead carries multiple electrodes 26 arranged in an array. The IPG 14 includes pulse generation circuitry that delivers electrical stimulation energy in the form of, for example, a pulsed electrical waveform (i.e., a temporal series of electrical pulses) to the electrode array 26 in accordance with a set of stimulation parameter values. The implantable pulse generator can be implanted into a patient's body, for example, below the patient's clavicle area or within the patient's abdominal cavity or at any other suitable site. The implantable pulse generator 14 can have multiple stimulation channels which may be independently programmable to control the magnitude of the current stimulus from each channel. In some embodiments, the implantable pulse generator 14 can have any suitable number of stimulation channels including, but not limited to, 4, 6, 8, 12, 16, 32, or more stimulation channels. The implantable pulse generator 14 can have one, two, three, four, or more connector ports, for receiving the terminals of the leads and/or lead extensions.

The ETS 20 may also be physically connected, optionally via the percutaneous lead extensions 28 and external cable 30, to the stimulation leads 12. The ETS 20, which may have similar pulse generation circuitry as the IPG 14, also delivers electrical stimulation energy in the form of, for example, a pulsed electrical waveform to the electrode array 26 in accordance with a set of stimulation parameter values. One difference between the ETS 20 and the IPG 14 is that the ETS 20 is often a non-implantable device that is used on a trial basis after the neurostimulation leads 12 have been implanted and prior to implantation of the IPG 14, to test the responsiveness of the stimulation that is to be provided. Any functions described herein with respect to the IPG 14 can likewise be performed with respect to the ETS 20.

The RC 16 may be used to telemetrically communicate with or control the IPG 14 or ETS 20 via a uni- or bi-directional wireless communications link 32. Once the IPG 14 and neurostimulation leads 12 are implanted, the RC 16 may be used to telemetrically communicate with or control the IPG 14 via a uni- or bi-directional communications link 34. Such communication or control allows the IPG 14, for example, to be turned on or off and to be programmed with different stimulation parameter sets. The IPG 14 may also be operated to modify the programmed stimulation parameter values to actively control the characteristics of the electrical stimulation energy output by the IPG 14. In at least some embodiments, the CP 18 (or RC 16 or other programming device) allows a user, such as a clinician, the ability to program stimulation parameter values for the IPG 14 and ETS 20 in the operating room and in follow-up sessions. Alternately, or additionally, in at least some embodiments, stimulation parameter values can be programed via wireless communications (e.g., Bluetooth) between the RC 16 (or other external device such as a hand-held electronic device like a mobile phone, tablet, or the like) and the IPG 14.

The CP 18 may perform this function by indirectly communicating with the IPG 14 or ETS 20, through the RC 16, via a wireless communications link 36. Alternatively, the CP 18 may directly communicate with the IPG 14 or ETS 20 via a wireless communications link (not shown). In at least some embodiments, the stimulation parameter values provided by the CP 18 are also used to program the RC 16, so that the stimulation parameter values can be subsequently modified by operation of the RC 16 in a stand-alone mode (i.e., without the assistance of the CP 18). The CP 18 or RC 16 can be any suitable device including, but not limited to, a computer or other computing device, laptop, mobile device (for example, a mobile phone or tablet), or the like or any combination thereof. The CP 18 or RC 16 can include software applications for interacting with the IPG 14 or ETS 20 and for programming the IPG 14 or ETS 20.

Additional examples of the RC 16, CP 18, ETS 20, and external charger 22 can be found in the references cited herein as well as U.S. Pat. Nos. 6,895,280; 6,181,969; 6,516,227; 6,609,029; 6,609,032; 6,741,892; 7,949,395; 7,244,150; 7,672,734; and 7,761,165; 7,974,706; 8,175,710; 8,224,450; and 8,364,278; and U.S. Patent Application Publication No. 2007/0150036, all of which are incorporated herein by reference in their entireties.

Figure 2:
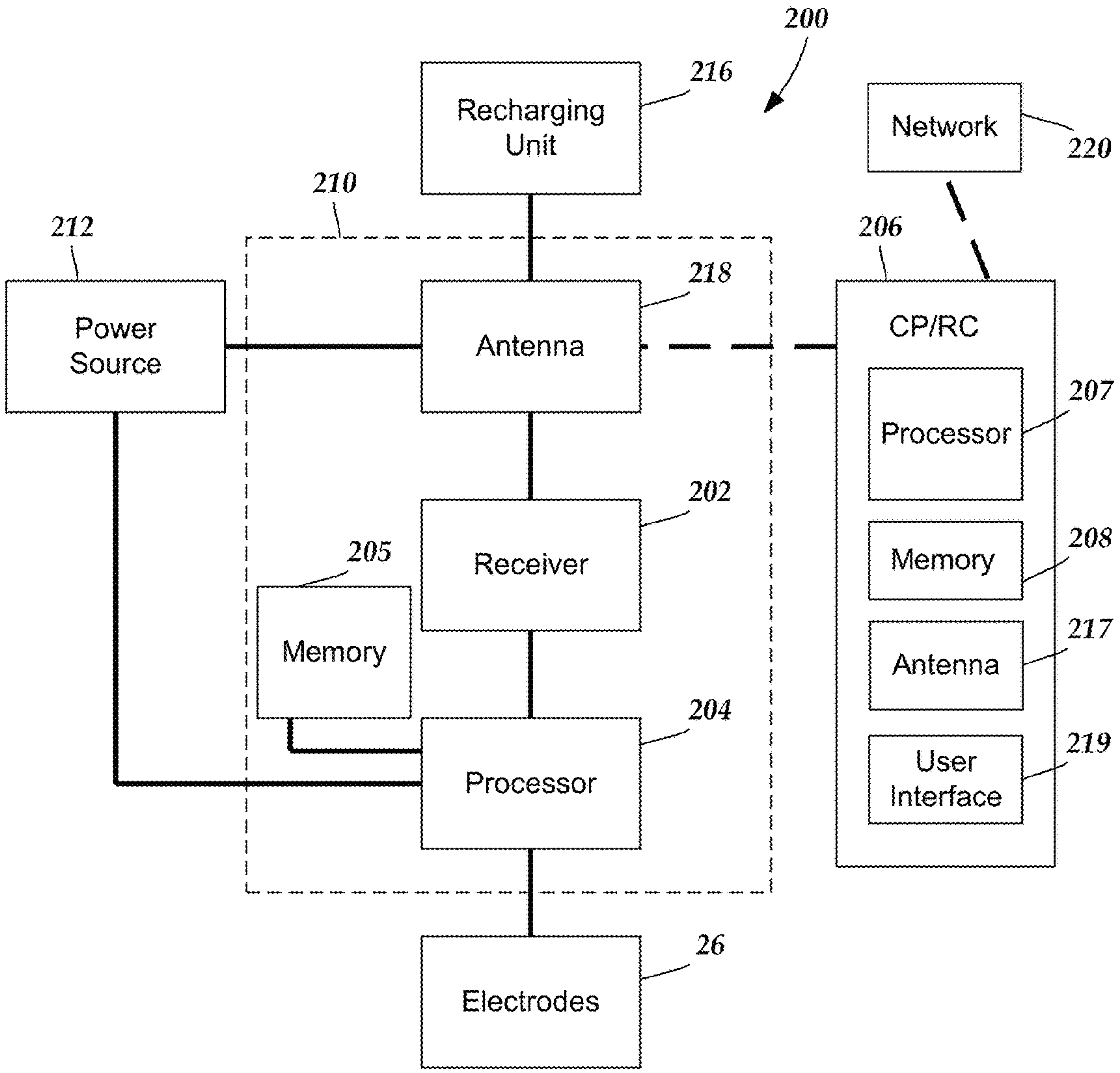
FIG. 2 is a block diagram of elements of an electrical stimulation system.

FIG. 2 is a schematic overview of one embodiment of components of an electrical stimulation system 200 including an electronic subassembly 210 disposed within an IPG 14 (FIG. 1). It will be understood that the electrical stimulation system can include more, fewer, or different components and can have a variety of different configurations including those configurations disclosed in the stimulator references cited herein.

The IPG 14 (FIG. 1) can include, for example, a power source 212, antenna 218, receiver 202, processor 204, and memory 205. Some of the components (for example, power source 212, antenna 218, receiver 202, processor 204, and memory 205) of the electrical stimulation system can be positioned on one or more circuit boards or similar carriers within a sealed housing of the IPG 14 (FIG. 1), if desired. Unless indicated otherwise, the term "processor" refers to both embodiments with a single processor and embodiments with multiple processors.

An external device, such as a CP or RC 206, can include a processor 207, memory 208, an antenna 217, and a user interface 219. The user interface 219 can include, but is not limited to, a display screen on which a digital user interface can be displayed and any suitable user input device, such as a keyboard, touchscreen, mouse, track ball, or the like or any combination thereof.

Any power source 212 can be used including, for example, a battery such as a primary battery or a rechargeable battery. Examples of other power sources include super capacitors, nuclear or atomic batteries, mechanical resonators, infrared collectors, thermally-powered energy sources, flexural powered energy sources, bioenergy power sources, fuel cells, bioelectric cells, osmotic pressure pumps, and the like including the power sources described in U.S. Pat. No. 7,437,193, incorporated herein by reference in its entirety.

As another alternative, power can be supplied by an external power source through inductive coupling via the antenna 218 or a secondary antenna. The external power source can be in a device that is mounted on the skin of the user or in a unit that is provided near the user on a permanent or periodic basis.

If the power source 212 is a rechargeable battery, the battery may be recharged using the antenna 218, if desired. Power can be provided to the battery for recharging by inductively coupling the battery through the antenna to a recharging unit 216 external to the user. Examples of such arrangements can be found in the references identified above.

In one embodiment, electrical current is emitted by the electrodes 26 on the lead body to stimulate nerve fibers, muscle fibers, or other body tissues near the electrical stimulation system. A processor 204 is generally included to control the timing and electrical characteristics of the electrical stimulation system. For example, the processor 204 can, if desired, control one or more of the timing, frequency, amplitude, width, and waveform of the pulses. In addition, the processor 204 can select which electrodes can be used to provide stimulation, if desired. In some embodiments, the processor 204 may select which electrode(s) are cathodes and which electrode(s) are anodes. In some embodiments, the processor 204 may be used to identify which electrodes provide the most useful stimulation of the desired tissue. Instructions for the processor 204 can be stored on the memory 205. Instructions for the processor 207 can be stored on the memory 208.

Any processor 204 can be used for the IPG and can be as simple as an electronic device that, for example, produces pulses at a regular interval or the processor can be capable of receiving and interpreting instructions from the CP/RC 206 (such as CP 18 or RC 16 of FIG. 1) that, for example, allows modification of pulse characteristics. In the illustrated embodiment, the processor 204 is coupled to a receiver 202 which, in turn, is coupled to the antenna 218. This allows the processor 204 to receive instructions from an external source to, for example, direct the pulse characteristics and the selection of electrodes, if desired. Any suitable processor 207 can be used for the CP/RC 206.

Any suitable memory 205, 208 can be used including computer-readable storage media may include, but is not limited to, volatile, nonvolatile, non-transitory, removable, and non-removable media implemented in any method or technology for storage of information, such as computer readable instructions, data structures, program modules, or other data. Examples of computer-readable storage media include, but are not limited to, RAM, ROM, EEPROM, flash memory, or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a processor.

In one embodiment, the antenna 218 is capable of receiving signals (e.g., RF signals) from an antenna 217 of a CP/RC 206 (see, CP 18 or RC 16 of FIG. 1) which is programmed or otherwise operated by a user. The signals sent to the processor 204 via the antenna 218 and receiver 202 can be used to modify or otherwise direct the operation of the electrical stimulation system. For example, the signals may be used to modify the pulses of the electrical stimulation system such as modifying one or more of pulse width, pulse frequency, pulse waveform, and pulse amplitude. The signals may also direct the electrical stimulation system 200 to cease operation, to start operation, to start signal acquisition, to stop signal acquisition, to start charging the battery, or to stop charging the battery. In other embodiments, the stimulation system does not include an antenna 218 or receiver 202 and the processor 204 operates as programmed.

Optionally, the electrical stimulation system 200 may include a transmitter (not shown) coupled to the processor 204 and the antenna 218 for transmitting signals back to the CP/RC 206 or another unit capable of receiving the signals. For example, the electrical stimulation system 200 may transmit signals indicating whether the electrical stimulation system 200 is operating properly or not or indicating when the battery needs to be charged or the level of charge remaining in the battery. The processor 204 may also be capable of transmitting information about the pulse characteristics so that a user or clinician can determine or verify the characteristics.

Transmission of signals can occur using any suitable method, technique, or platform including, but not limited to, inductive transmission, radiofrequency transmission, Bluetooth™, Wi-Fi, cellular transmission, near field transmission, infrared transmission, or the like or any combination thereof. In addition, the IPG 14 can be wirelessly coupled to the RC 16 or CP 18 using any suitable arrangement include direct transmission or transmission through a network, such as a local area network, wide area network, the Internet, or the like or any combination thereof. The CP 18 or RC 16 may also be capable of coupling to, and sending data or other information to, a network 220, such as a local area network, wide area network, the Internet, or the like or any combination thereof.

At least some of the stimulation electrodes can take the form of segmented electrodes that extend only partially around the perimeter (for example, the circumference) of the lead. These segmented electrodes can be provided in sets of electrodes, with each set having electrodes circumferentially distributed about the lead at a particular longitudinal position.

Figure 3A:
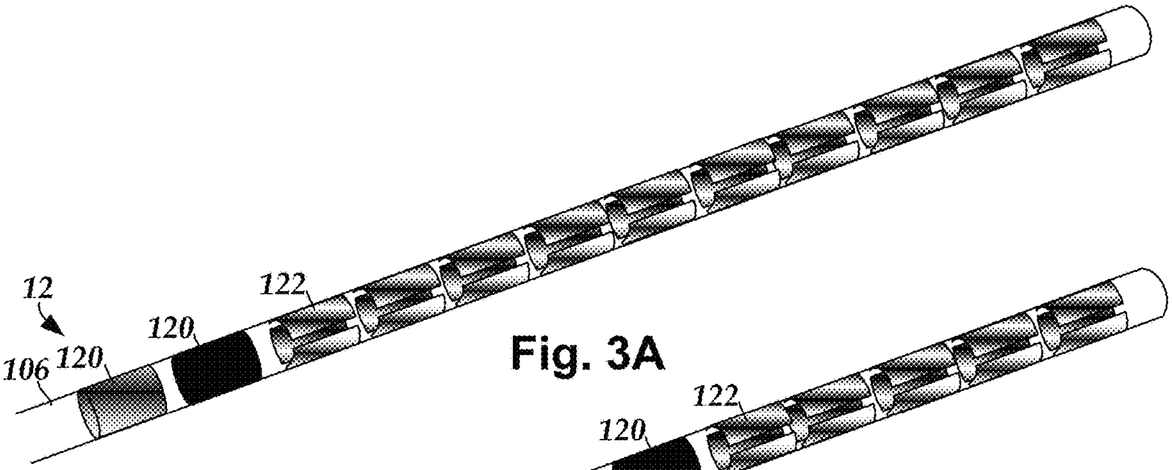
FIG. 3A is a schematic perspective view of a distal portion of one embodiment of an electrical stimulation lead with segmented electrodes.
Figure 3B:
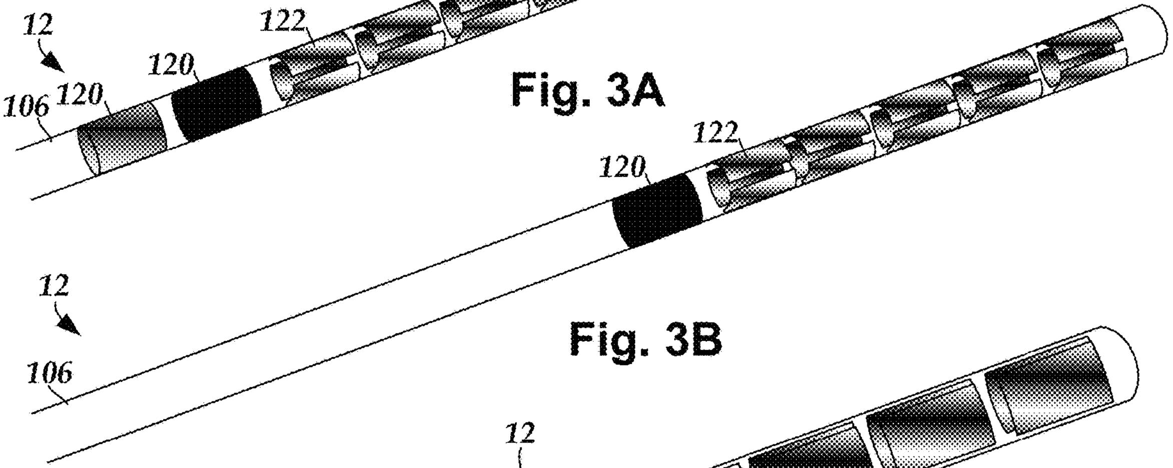
FIG. 3B is a schematic perspective view of a distal portion of another embodiment of an electrical stimulation lead with segmented electrodes.
Figure 3C:
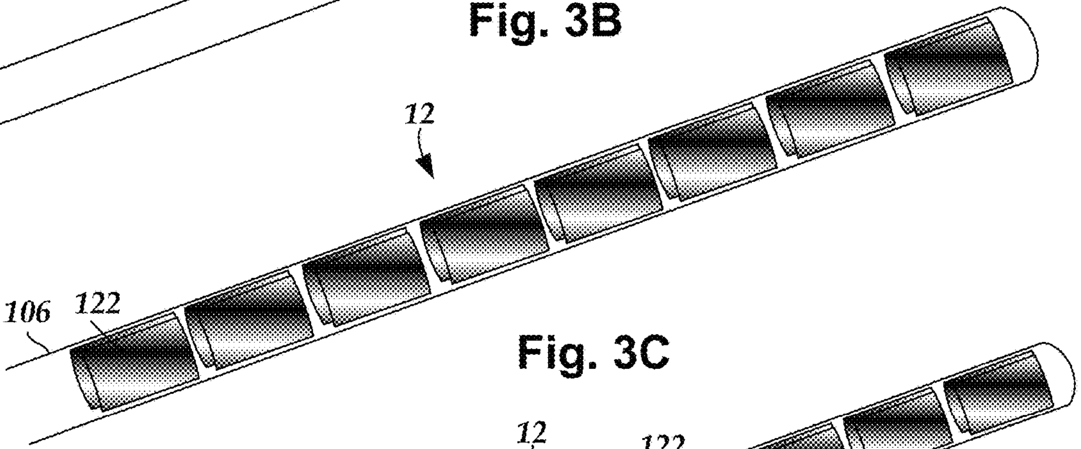
FIG. 3C is a schematic perspective view of a distal portion of a third embodiment of an electrical stimulation lead with segmented electrodes.
Figure 3D:
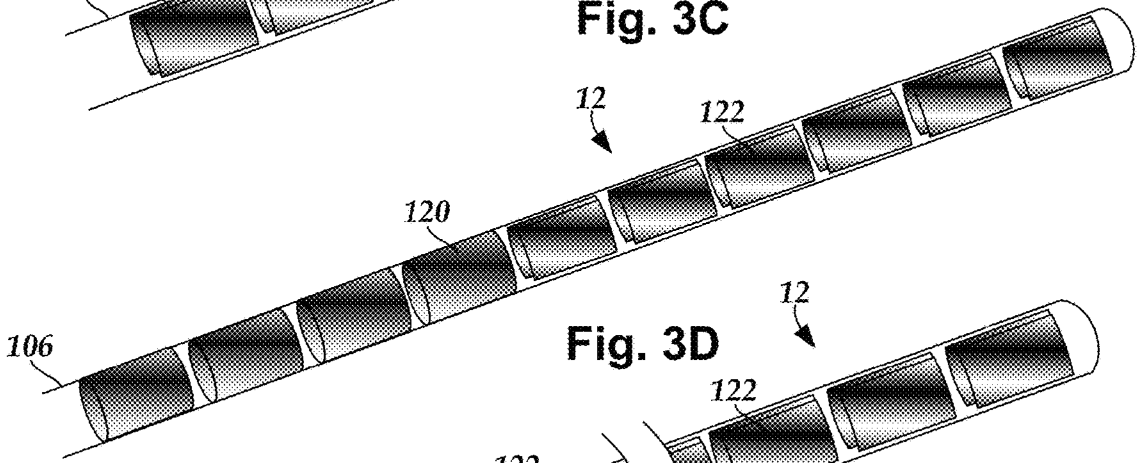
FIG. 3D is a schematic perspective view of a distal portion of a fourth embodiment of an electrical stimulation lead with segmented electrodes.
Figure 3E:
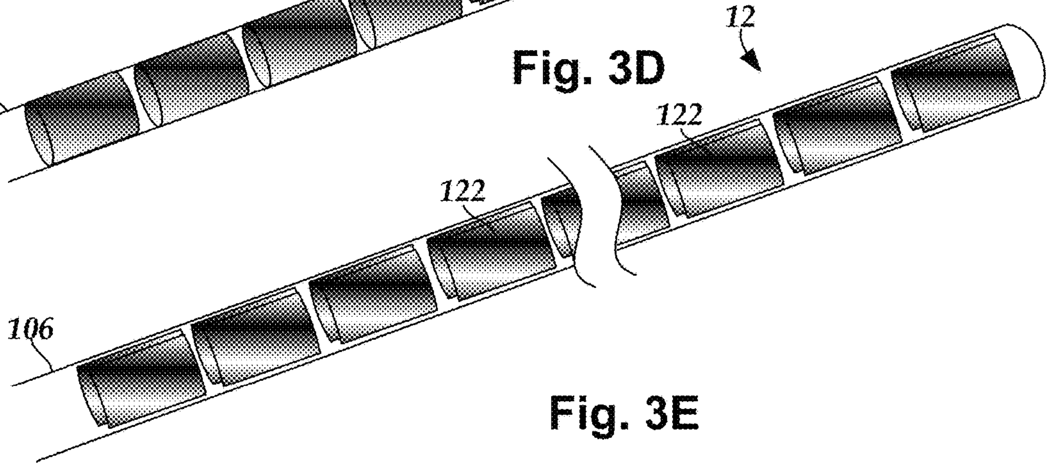
FIG. 3E is a schematic perspective view of a distal portion of a fifth embodiment of an electrical stimulation lead with segmented electrodes.

In FIGS. 3A, 3B, and 3D the electrodes are shown as including both ring electrodes 120 and segmented electrodes 122. In some embodiments, the electrodes are all segmented electrode 122, as illustrated in FIGS. 3C and 3E. The segmented electrodes 122 of FIG. 3A are in sets of three, where the three segmented electrodes of a particular set are electrically isolated from one another and are circumferentially offset along the lead 12. Any suitable number of segmented electrodes can be formed into a set including, for example, two, three, four, or more segmented electrodes. The lead 12 of FIG. 3A has thirty segmented electrodes 122 (ten sets of three electrodes each) and two ring electrodes 120 for a total of 32 electrodes.

Segmented electrodes can be used to direct stimulus current to one side, or even a portion of one side, of the lead. When segmented electrodes are used in conjunction with an implantable pulse generator that delivers current stimulus, current steering can be achieved to deliver the stimulus more precisely to a position around an axis of the lead (i.e., radial positioning around the axis of the lead). Segmented electrodes may provide for superior current steering than ring electrodes because target structures in deep brain stimulation are not typically symmetric about the axis of the distal electrode array. Instead, a target may be located on one side of a plane running through the axis of the lead. Through the use of a segmented electrode array, current steering can be performed not only along a length of the lead but also around a perimeter of the lead. This provides precise three-dimensional targeting and delivery of the current stimulus to neural target tissue, while potentially avoiding stimulation of other tissue.

FIG. 3A illustrates a 32-electrode lead 12 with a lead body 106 and two ring electrodes 120 proximal to thirty segmented electrodes 122 arranged in ten sets of three segmented electrodes each. In the illustrated embodiments, the ring electrodes 120 are proximal to the segmented electrodes 122. In other embodiments, the ring electrodes 120 can be proximal to, or distal to, or any combination thereof.

Any number of segmented electrodes 122 may be disposed on the lead body including, for example, one, two, three, four, five, six, seven, eight, nine, ten, eleven, twelve, thirteen, fourteen, fifteen, sixteen, twenty, twenty-four, twenty-eight, thirty, thirty-two, or more segmented electrodes 122. It will be understood that any number of segmented electrodes 122 may be disposed along the length of the lead body. A segmented electrode 122 typically extends only 75%, 67%, 60%, 50%, 40%, 33%, 25%, 20%, 17%, 15%, or less around the circumference of the lead.

The segmented electrodes 122 may be grouped into sets of segmented electrodes, where each set is disposed around a circumference of the lead 12 at a particular longitudinal portion of the lead 12. The lead 12 may have any number of segmented electrodes 122 in a given set of segmented electrodes. The lead 12 may have one, two, three, four, five, six, seven, eight, or more segmented electrodes 122 in a given set. The lead 12 may have any number of sets of segmented electrode including, but not limited to, one, two, three, four, five, six, eight, ten, twelve, fifteen, sixteen, twenty, or more sets. The segmented electrodes 122 may be uniform, or vary, in size and shape. In some embodiments, the segmented electrodes 122 are all of the same size, shape, diameter, width or area or any combination thereof. In some embodiments, the segmented electrodes 122 of each circumferential set (or even all segmented electrodes disposed on the lead 12) may be identical in size and shape.

Each set of segmented electrodes 122 may be disposed around the circumference of the lead body to form a substantially cylindrical shape around the lead body. The spacing between individual electrodes of a given set of the segmented electrodes may be the same, or different from, the spacing between individual electrodes of another set of segmented electrodes on the lead 12. In at least some embodiments, equal spaces, gaps, or cutouts are disposed between each segmented electrode 122 around the circumference of the lead body. In other embodiments, the spaces, gaps, or cutouts between the segmented electrodes 122 may differ in size or shape. In other embodiments, the spaces, gaps, or cutouts between segmented electrodes 122 may be uniform for a particular set of the segmented electrodes 122, or for all sets of the segmented electrodes 122. The sets of segmented electrodes 122 may be positioned in irregular or regular intervals along a length of the lead body.

The electrodes of the lead 12 are typically disposed in, or separated by, a non-conductive, biocompatible material of a lead body 106 including, for example, silicone, polyurethane, and the like or combinations thereof. The lead body 106 may be formed in the desired shape by any process including, for example, extruding, molding (including injection molding), casting, and the like. Electrodes and connecting wires can be disposed onto or within a lead body either prior to or subsequent to a molding or casting process. The non-conductive material typically extends from the distal end of the lead body 106 to the proximal end of the lead body 106.

FIG. 3B to 3E illustrate other embodiments of leads with segmented electrodes 122. FIG. 3B illustrates a sixteen electrode lead 12 having one ring electrode 120 that is proximal to five sets of three segmented electrodes 122 each. FIG. 3C illustrates a sixteen electrode lead 12 having eight sets of two segmented electrodes 122 each. As illustrated in FIG. 3C, an embodiment of a lead 12 does not necessarily include a ring electrode. FIG. 3D illustrates a sixteen electrode lead 12 having four ring electrodes 120 that are proximal to six sets of two segmented electrodes 122 each. FIG. 3E illustrates a thirty-two electrode lead 12 having sixteen sets of two segmented electrodes 122 each (for clarity of illustration, not all of the electrodes are shown). It will be recognized that any other electrode combination of ring electrodes, segmented electrodes, or both types of electrodes can be used.

When the lead 12 includes both ring electrodes 120 and segmented electrodes 122, the ring electrodes 120 and the segmented electrodes 122 may be arranged in any suitable configuration. For example, when the lead 12 includes two or more ring electrodes 120 and one or more sets of segmented electrodes 122, the ring electrodes 120 can flank the one or more sets of segmented electrodes 122. Alternately, the two or more ring electrodes 120 can be disposed proximal to the one or more sets of segmented electrodes 122 or the two or more ring electrodes 120 can be disposed distal to the one or more sets of segmented electrodes 122.

The electrodes 120, 122 may have any suitable longitudinal length including, but not limited to, 2, 3, 4, 4.5, 5, or 6 mm. The longitudinal spacing between adjacent electrodes 120, 122 may be any suitable amount including, but not limited to, 1, 2, or 3 mm, where the spacing is defined as the distance between the nearest edges of two adjacent electrodes. In some embodiments, the spacing is uniform between longitudinally adjacent electrodes along the length of the lead. In other embodiments, the spacing between longitudinally adjacent electrodes may be different or non-uniform along the length of the lead.

Examples of leads with segmented electrodes include U.S. Patent Application Publications Nos. 2010/0268298; 2011/0005069; 2011/0078900; 2011/0130803; 2011/0130816; 2011/0130817; 2011/0130818; 2011/0078900; 2011/0238129; 2011/0313500; 2012/0016378; 2012/0046710; 2012/0071949; 2012/0165911; 2012/0197375; 2012/0203316; 2012/0203320; 2012/0203321; 2013/0197602; 2013/0261684; 2013/0325091; 2013/0317587; 2014/0039587; 2014/0353001; 2014/0358209; 2014/0358210; 2015/0018915; 2015/0021817; 2015/0045864; 2015/0021817; 2015/0066120; 2013/0197424; 2015/0151113; 2014/0358207; and U.S. Pat. No. 8,483,237, all of which are incorporated herein by reference in their entireties. A lead may also include a tip electrode and examples of leads with tip electrodes include at least some of the previously cited references, as well as U.S. Patent Application Publications Nos. 2014/0296953 and 2014/0343647, all of which are incorporated herein by reference in their entireties. A lead with segmented electrodes may be a directional lead that can provide stimulation in a particular direction using the segmented electrodes.

Instead of, or in addition to, the electrodes 120, 122, a lead 12 can include one or more optical emitters (which can, for example, replace any of the electrodes 120, 122). Each optical emitter can be a light source (for example, a light emitting diode (LED), light emitting transistor (LET), laser diode, a vertical cavity side-emitting laser (VCSEL), an organic light emitting diode (OLED), an organic light emitting transistor (OLET), a lamp, or the like) or can be a light emission region of an optical waveguide (for example, a fiber optic, optical fiber, lens, or any other suitable conveyance of light) or the like. Examples of leads with optical emitters can be found at U.S. Pat. Nos. 9,415,154; 10,335,607; 10,625,072; and 10,814,140 and U.S. Patent Application Publications Nos. 2013/0317572; 2013/0317573; 2017/0259078; 2017/0225007; 2018/0110971; 2018/0369606; 2018/0369607; 2019/0209849; 2019/0209834; 2020/0094047; 2020/0155584; 2020/0376262; 2021/0008388;

2021/0008389; 2021/0016111; and 2022/0072329; all of which are incorporated herein by reference in their entireties.

The following discussion uses electrical stimulation systems with electrodes as examples. It will be understood that the optical stimulation or modulation systems or electrical/optical stimulation systems can be used in place of the example electrical stimulation systems. Thus, a stimulation system can include electrodes, optical emitters, or any combination thereof. It will be understood that any suitable type of stimulation can be used including, but not limited to, deep brain stimulation, spinal cord stimulation, vagal stimulation, peripheral nerve stimulation, or the like or any combination thereof.

In at addition, the following discussion uses Parkinson's disease, as an example of a disease or disorder for treatment, as well as dyskinesia and freezing of gait (FOG), as examples of symptoms or side effects. It will be understood that the methods and systems described herein can be used to treat other diseases, disorders, and symptoms and to address other side effects.

The sensing or monitoring of one or more symptoms, therapeutic effects, or side effects can be used to modify, adjust, or alter (or suggest modifications, adjustments, or alterations of) stimulation to enhance therapeutic effects or reduce side effects or symptoms. As an example, deep brain stimulation can be used to treat Parkinson's Disease (or other diseases and disorders) and provide therapeutic effects to reduce symptoms or side effects, such as dyskinesia or freezing of gait (FOG). Although some sets of stimulation parameter values can alleviate or prevent dyskinesia or FOG, other sets of stimulation parameter values may exacerbate dyskinesia or FOG while addressing other Parkinson's symptoms or providing other therapeutic effects. Stimulation parameter values may be selected as a compromise or combination between treatments for different symptoms.

In some instances, the magnitude or effect of a symptom, such as dyskinesia, or a therapeutic effect or side effect (or even the existence of a side effect) may increase or decrease for any of a variety of reasons. It may be desirable to modify, adjust, or alter stimulation in response to the change in the symptom, therapeutic effect, or side effect or any combination thereof. In addition, the presence or administration of medication, or changes in the dosage, dosage interval, or time of effect of the medication, may alter a patient's response to stimulation, which may include increasing or decreasing the magnitude of a symptom, therapeutic effect, or side effect or may include a side effect manifesting or becoming existent.

Figure 4:
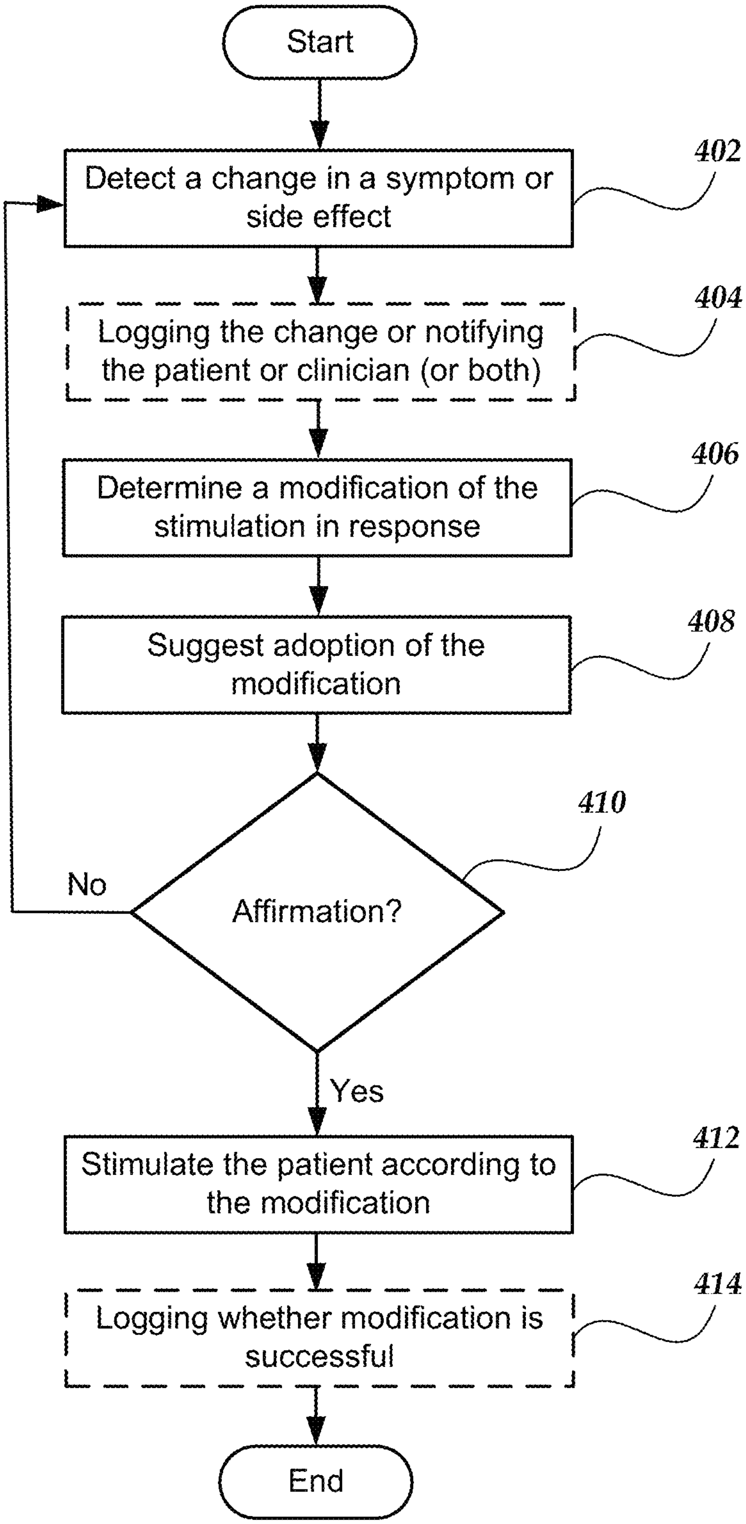
FIG. 4 is a flowchart of one embodiment of a method for adapting stimulation by a stimulation system to changes in a symptom, therapeutic effect, or side effect.

FIG. 4 illustrates one embodiment of a method for adapting stimulation by a stimulation system to changes in a symptom, therapeutic effect, or side effect. Examples of changes can include, but are not limited to, an increase or decrease in the magnitude of a symptom, therapeutic effect, or side effect; a change in the presentation of a symptom, therapeutic effect, or side effect; or manifestation or emergence of a symptom, therapeutic effect, or side effect. Examples of the symptom, therapeutic effect, or side effect include dyskinesia, freezing of gait, nausea, headache, dizziness, tingling or numbness in limbs, muscle contraction or twitching, fatigue or sleepiness, mood changes, anxiety, irritability, vision problems, cognitive or memory problems, cognitive impairment, paresthesia, affective disorder, akinesia, risk of falls, sleep or waking disturbance, apathy, depression, mania, punding or other compulsive disorders, dysarthria or other speech difficulties, changes in voice tone, hyperhidrosis, non-motor symptoms, or the like or any combination thereof.

In step 402, a change in a symptom of a disease or disorder or of a side effect of stimulation is detected or otherwise determined by the stimulation system. In at least some embodiments, a stimulation system can identify, monitor, or measure at least one symptom, therapeutic effect, or side effect (or an indicator of the symptom, therapeutic effect, or side effect). In at least some embodiments, a stimulation system can receive information from an external device to facilitate the identification, monitoring, or measurement of at least one symptom, therapeutic effect, or side effect (or an indicator of the symptom, therapeutic effect, or side effect). Any suitable method or device can be used for identifying, monitoring, or measuring including, for example, the use of one or more external or internal sensors; patient input (for example, information input by the patient into a remote control, which may be directed or non-directed); changes to the stimulation initiated by the patient, a clinician, or other individual; or the like or any combination thereof.

In at least some embodiments, a symptom of a disease/disorder, a therapeutic effect, or a side effect of stimulation is detected using a sensor disposed on or within the patient. Sensors, or other monitoring devices, can be used to identify dyskinesia, FOG, or other symptoms, therapeutic effects, or side effects. Sensors can be external, such as a smart watch, smart band, smart ring, smart phone or other smart device, shoe sensor, any other suitable wearable sensor, axially-located sensor, accelerometer, pressure sensor, temperature sensor, position sensor, auditory device. A sensor can be internal, such as implanted electrical, magnetic, or chemical sensors.

In at least some embodiments, a sensor can be selected to monitor or measure any suitable biosignal, chemical, or motion. As an example, a biosignal sensor can be used to monitor or measure local field potentials (LFP), evoked potential (EP), deep brain stimulation (DBS) local evoked potential (DLEP), evoked resonant neural activity (ERNA), ECG, EKG, EMG, electrocochleograph (ECOG), heart rate, blood pressure, electrical signals traversing the spinal cord or a nerve or group of nerves, any other suitable biological signals, or the like or any combination thereof. A chemical sensor can be used to monitor or measure, for example, any suitable biochemical(s). A motion sensor may be used to monitor, for example, tremor, gait, motion of particular body parts, or activities (for example, walking, running, sleeping, or the like), slowness of movement (e.g., bradykinesia), or any other suitable patient movement or motion, or the like or any combination thereof.

In at least some embodiments, an internal sensor can be part of the lead or control module. For example, the electrodes on a lead can also be used for recording a LFP, ERNA, ECG, EKG, EMG, electrocochleograph (ECOG), heart rate, ECG, or other electrical signals generated by or in the tissue of the patient.

In at least some embodiments, the sensitivity of the stimulation system to changes can be set or user selectable. For example, in order to suggest or initiate a modification of stimulation parameter value(s), the stimulation system can have a set, or user-selected, requirement that the change correspond to a threshold magnitude or score, or a threshold amount of change, for the symptom, therapeutic effect, or side effect or for an indicator of the symptom, therapeutic effect, or side effect). Additionally or alternatively, the stimulation system can have a set, or user-selected, requirement for a specific period of time (for example, 1, 5, 10, 15, or 30 minutes or 1, 2, 3, 4, or 6 or more hours) during which the determined change in the symptom, therapeutic effect, or side effect is present in order to suggest or initiate a modification of stimulation parameter value(s). In at least some embodiments, the stimulation system may also detect when the change or the symptom or side effect is no longer present and then revert to the early stimulation parameter value(s).

In at least some embodiments, the stimulation system can have a set, or user-selectable, period of time (for example, 1, 2, 3, 4, 6, or more hours) before another suggestion or initiation of a modification of stimulation parameter value(s) can occur. In at least some embodiments, this period of time may depend on the estimated or expected response rate of the symptom, therapeutic effect, or side effect to changes in stimulation. In at least some embodiments, the stimulation system can have a set, or user-selectable, period of time (for example, 1, 2, 3, 4, 6, or more hours) during which a transition to the modification is made such, as for example, ramping from the unmodified stimulation parameter value(s) to the modified stimulation parameter value(s); changing the duty cycle of the stimulation; or alternating between the modified stimulation parameter value(s) and the unmodified stimulation parameter value(s) (with, in at least some embodiments, increasing application of the modified stimulation parameter value(s)).

In at least some embodiments, the stimulation system can have a set, or user-selectable, limit on the modification of the stimulation parameter value(s). For example, the stimulation system may limit the change in amplitude, the change in the direction of stimulation (for example, rotation of the stimulation about the lead), the change in the movement of the stimulation up or down the lead (for example, change in the electrode selection up or down the lead), or the like or any combination thereof.

In at least some embodiments, there may be multiple thresholds or interconnected rules, requirements, or limits for any of these set, or user-selectable, parameters. As an example, the stimulation system may suggest or initiate a modification of stimulation parameter value(s) when a particular symptom or side effect increases by 5% and may limit another modification to occurring no sooner than five minutes later. The stimulation system in this example may have another rule that if the particular symptom or side effect increases by 10% then the five minute time limit is removed.

In optional step 404 (which can occur after any of steps 402, 406, or 408), the detected or determined change in the symptom, therapeutic effect, or side effect is logged into a memory of any suitable component of the stimulation system, such as, for example, the implantable pulse generator, remote control, clinician programmer, or any other suitable device, or to a memory external to the system. In at least in some embodiments, the stimulation system also logs the symptom, therapeutic effect, or side effect. Other information that can be logged includes, for example, the time of the change, whether medication was administered prior to the change, the time at which the medication was administered, medication dosage, medication dosage interval, a proposed modification of stimulation parameter values (see, step 406), the magnitude of the change, the current stimulation parameter values, or the like or any combination thereof.

Additionally or alternatively, in optional step 404, the stimulation system can notify the patient, a clinician, a caregiver, or any other suitable individual or any combination thereof of the change in the symptom, therapeutic effect, or side effect. For example, the patient or caregiver may be notified on the remote control or a smartphone that receives information from the system or sensor(s). The clinician may be notified by the clinician programmer or by the system sending a message to the clinician via email, text, phone call, or any other suitable communication method or any combination thereof. The notification may include any of the information that is described above with respect to logging and may include, for example, a predicted outcome of the modified stimulation, a time since a last notification or modification, or the like or any combination thereof.

In at least some embodiments, the patient, clinician, caregiver, or any other suitable individual or any combination thereof is notified on a periodic basis (for example, every 1, 2, 4, 6, or 12 hours or every day or week or any other suitable time period). In at least some embodiments, a notification after modification of the stimulation, as described below, to indicate or confirm the outcome of the modification.

In step 406, in response to detection of the change in the symptom, side effect or therapeutic effect, a modification of one or more stimulation parameter values of the stimulation is determined by the stimulation system to adapt to the change in the symptom, side effect, or therapeutic effect. In this manner, the stimulation system can provide for adaptive adjustment of the stimulation to the sensed symptom(s), therapeutic effect(s), or side effect(s). It will be understood that modification of one or more stimulation parameters can be performed by selecting a different stimulation program or altering an existing or current stimulation program.

In at least some embodiments, the stimulation system may utilize a set of preprogrammed rules to determine the modification. In at least some embodiments, the stimulation system may utilize recorded results (for example, recorded clinical effects) of previous stimulations to the patient or to other patients to determine the modification. Examples of such information can include neuroimaging and electrophysical information from the patient or from a population of patients or any combination thereof. Examples of methods for obtaining and recording clinical effects can be found at, for example, U.S. Pat. Nos. 9,227,074; 9,248,296; 9,358,398; 9,474,903; 10,071,249; 10,357,657; 10,369,364; 10,603,498; and 10,716,505; U.S. Patent Application Publications Nos. 2014/0243926; 2014/0276707; 2014/0277282; 2014/0277284; 2018/0264278; 2020/0376263; 2020/0398057; and 2021/0023374; U.S. patent application Ser. No. 18/075,835; and U.S. Provisional Patent Application Ser. Nos. 63/425,149 and 63/432,628, all of which are incorporated herein by reference in their entireties. Any other suitable method for determination of the modification can be used including, but not limited to those in any of the references cited herein including U.S. Pat. Nos. 8,326,433; 8,675,945; 8,831,731; 8,849,632; 8,958,615; 10,265,528; and 10,603,498; U.S. Patent Application Publications Nos. 2009/0287272; 2009/0287273; 2012/0314924; 2013/0116744; 2014/0122379; 2015/0066111; and 2022/0339448, all of which are incorporated herein by reference in their entireties.

As an example, the stimulation system may determine a modification to the stimulation parameter value(s) that moves the stimulation (via, for example, a change in electrode selection or electrode fractionalization) relative to the lead or that reduces the stimulation (via, for example, reducing the amplitude, pulse width, or pulse rate or any combination thereof) when the symptom or side effect is determined to be worse. (Electrode fractionalization is the relative distribution of the stimulation current or voltage among the electrodes of the lead.) Modification to the electrode selection or electrode fractionalization may, for example, move the stimulation distally or proximally relative to the lead or narrow/increase the circumferential extent of the stimulation or the like or any combination thereof. The stimulation system may determine a modification to the stimulation program that increases the stimulation (via, for example, increasing the amplitude, pulse width, or pulse rate or any combination thereof) when the symptom or side effect is alleviated. The stimulation system may take into account the magnitude of the symptom or side effect in selection of the new stimulation parameter values or stimulation program.

In at least some embodiments, the stimulation system may also include modifications that have been previously input or selected by a clinician or other individual to address a change in a particular symptom, side effect, therapeutic effect, or other circumstance (for example, previously input stimulation programs). The stimulation system can adopt the previously input modification which may include a rule or rules for circumstances for implementation of that modification.

In at least some embodiments, the modification may include changing the stimulation along one portion of the lead while maintaining the stimulation along another portion of the lead. In at least some embodiments, the modification can include initiating stimulation when stimulation was previously not provided; initiating stimulation to a particular anatomical region that is not currently being stimulated; or halting or reducing stimulation to a particular anatomical region. In at least some embodiments, the modification may include providing supplemental stimulation to the stimulation currently provided.

In step 408, adoption of the modification is suggested to the patient, clinician, caregiver, or the like or any combination thereof. In at least some embodiments, when the stimulation system provides a suggestion to modify the stimulation program to the patient, clinician, caregiver, or the like or any combination thereof, the system can request confirmation that the modification should be adopted. In at least some embodiments, the patient or caregiver can affirm the modification using the remote control, a smartphone, or any other suitable device. In at least some embodiments, the clinician can affirm the modification using the clinician programmer or any other suitable device. In at least some embodiments, notification of the modification is sufficient to initiate the modification.

In at least some embodiments, multiple sets of modifications may be determined and may include assessments of risk, effectiveness, or the like or any combination thereof. The individual(s) queried for adoption of the modification may be asked to select between the sets of modifications.

In at least some embodiments in which the suggested modification has been previously adopted, the stimulation system may skip steps 408 and 410 and proceed directly to step 412. In at least some embodiments, the stimulation system can include one or more rules regarding a threshold for "closeness" of a suggested modification and a previously adopted modification that may allow the stimulation system to skip steps 408 and 410 and proceed directly to step 412.

In step 410, it is determined whether the patient or clinician (or both) affirm or accept the modification. If no, then the procedure returns to step 402 or ends. If yes, then in step 412, the patient is stimulated using the modification of the one or more stimulation parameter values.

In optional step 414, it is determined whether the modification is successful and the result of that determination is logged on the stimulation system or elsewhere. As an example, a determination is made whether the modification of the one or more stimulation parameter values increases or decreases the symptom or side effect to evaluate success or lack of success. The determination may be made using any suitable method or device including the methods and devices described above for determining a change in the symptom, therapeutic effect, or side effect. The system may also log the magnitude of any change in the symptom, side effect, or therapeutic effect or any change of an indicator of the symptom, side effect, or therapeutic effect. The system may also log any other suitable information including the information described above with respect to step 404. In at least some embodiments, a stimulation effect may take time to manifest. The log include observations over a period of time and may identify effects that occur over the period of time.

The procedure may then repeat the steps until stimulation is terminated or until the system is directed to halt the procedure.

Figure 5:
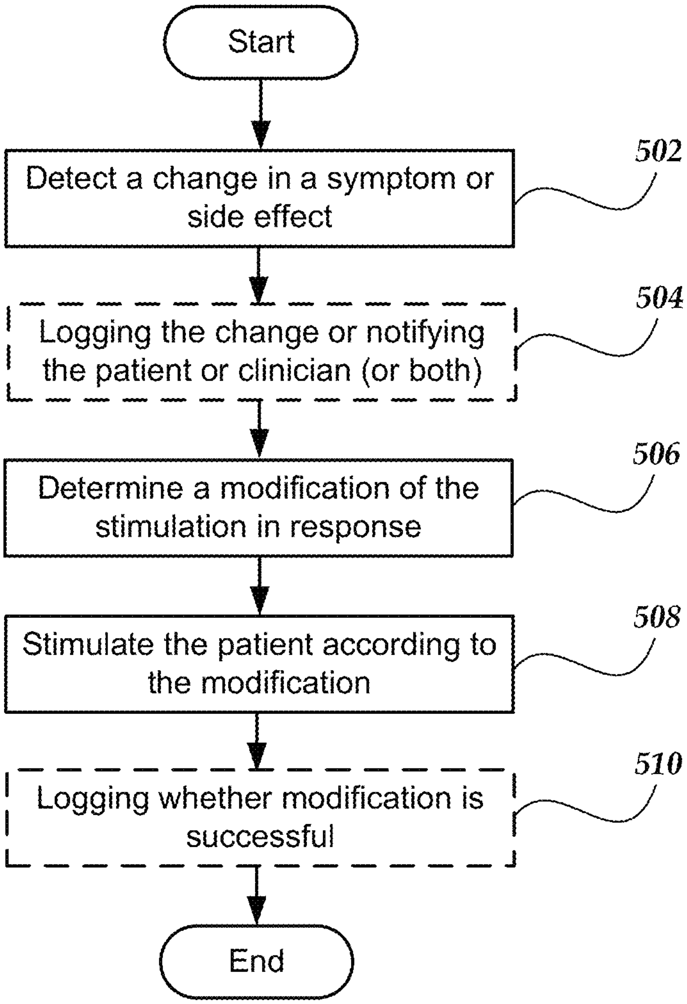
FIG. 5 is a flowchart of another embodiment of a method for adapting stimulation by a stimulation system to changes in a symptom, therapeutic effect, or side effect.

FIG. 5 illustrates another embodiment of a method for adapting stimulation by a stimulation system to changes in a symptom, therapeutic effect, or side effect. Steps 502, 504, 506, and 510 are the same as steps 402, 440, 406, and 414, respectively.

The method illustrated in FIG. 5 differs from the preceding method in that the modification of one or more of the stimulation parameter values is implemented automatically by the stimulation system, as illustrated in step 508. In at least some embodiments, the system allows, optionally without prompting, the patient, clinician, caregiver or the like or any combination thereof to reverse the modification. For example, when the patient is unsatisfied with the modified stimulation, the system can permit the patient to reverse the modification or otherwise change the stimulation.

In at least some embodiments, after the modification, the patient, clinician, caregiver, or the like or any combination thereof is informed of the change. In at least some embodiments, the informed individual(s) is/are requested to confirm the modification and, if not confirmed, the modification is reversed.

In at least some embodiments, the stimulation system records trends in stimulation program selection, modifications to stimulation parameter value(s), or the monitored level of at least one symptom, therapeutic effect, or side effect. As an example, when a symptom or side effect is detected or determined and a modification to one or more stimulation parameter values is initiated by the user, clinician, caregiver, or other individual or suggested or initiated by the stimulation system, the stimulation system can log the symptom or side effect (and, at least in some embodiments, the severity of the symptom or side effect) and the modification. Other information can be recorded, such as, for example, the time of the detection/determination of the symptom, therapeutic effect, or side effect, the time of the program change, the type of modifications made to the stimulation parameter value(s), the amount of change to the stimulation parameter value(s), administration of medication, time of the administration of medication, the results of stimulation using the modification (for example, decrease/increase in the symptom or side effect), or the like or any combination thereof.

Figure 6:
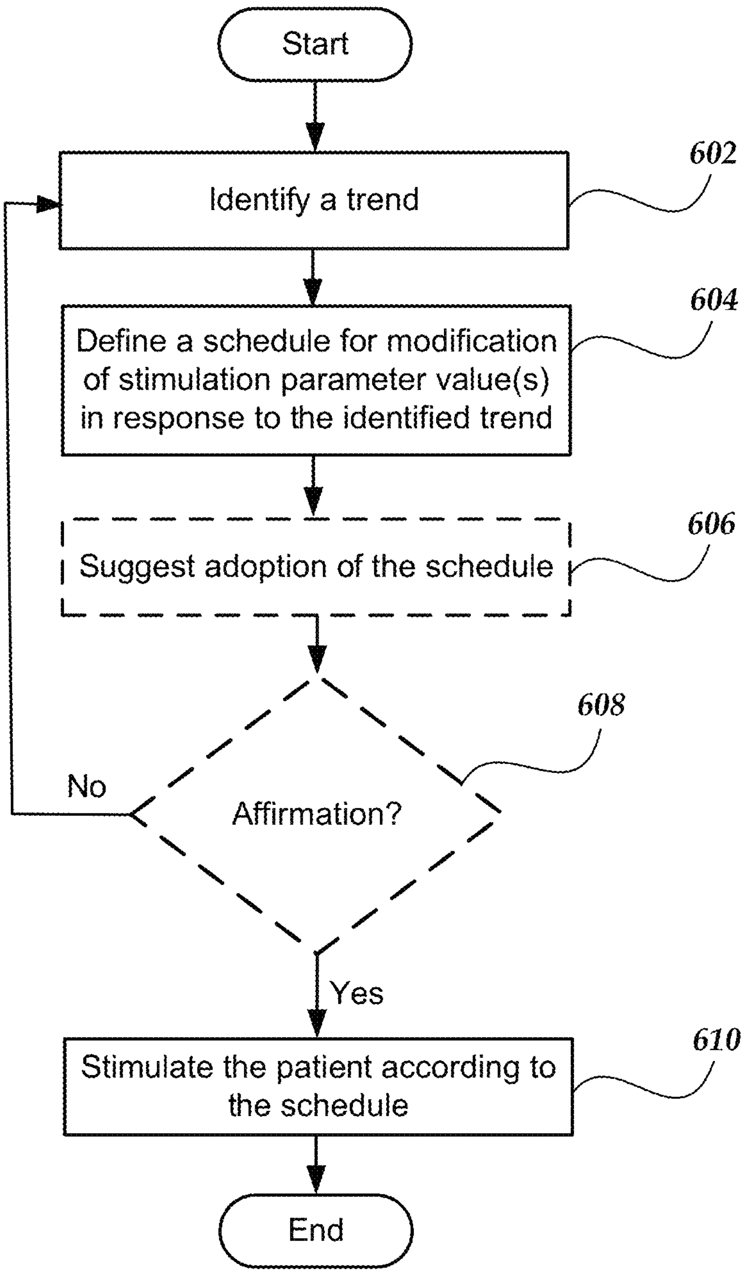
FIG. 6 is a flowchart of one embodiment of a method of modifying stimulation in response to an identified trend.

FIG. 6 illustrates one embodiment of a method of modifying stimulation in response to an identified trend. In step 602, the stimulation system, or an external system, can identify trends in the application or modification of specific stimulator parameter values generally or in response to a trigger event, such as, for example, changes in the symptom, therapeutic effect, or side effect; administration of medication; particular user activities or level of activity; particular time of day; or the like or any combination thereof. In at least some embodiments, the system can designate a modification as "successful" or "unsuccessful" (or any other equivalent words, numbers, or the like) based on the outcome of the stimulation, such as, for example, the decrease/increase of the symptom or side effect (or other symptoms or side effects or therapeutic effects or any combination thereof).

In step 604, in at least some embodiments, the stimulation system can define a schedule for suggesting, or automatically initiating, a modification of stimulation parameter value(s) based on the identified trend(s) (for example, in response to a trigger event). For example, when, over a course of time (for example, 1, 2, 5, or 10 days, 1, 2, or 4 weeks, 1, 2, 4, 6, or more months or any other suitable time period), the same or similar modifications to stimulation parameter value(s) are made or suggested under similar circumstances (for example, when the symptom or side effect increases, when medication is administered, or at the same time each day), the stimulation system can generate a schedule for modifying the stimulation parameter value(s) under specific conditions, such as detection/determination of the symptom or side effect, the administration of medication, specific times of the day, detection of specific activities, or the like or any combination thereof.

As an example, the stimulation system may identify a trend in the monitored level of at least one symptom, therapeutic effect, or side effect with administration of medication. The stimulation system may schedule the suggestion of, or automatically initiate, a different stimulation program to coincide with the administration of medication.

In optional step 606, adoption of the schedule is suggested to the patient, clinician, caregiver, or the like or any combination thereof. In at least some embodiments, when the stimulation system provides a suggested schedule to the patient, clinician, caregiver, or the like or any combination thereof, the system can request confirmation that the schedule should be adopted. In at least some embodiments, the patient or caregiver can affirm the schedule using the remote control, a smartphone, or any other suitable device. In at least some embodiments, the clinician can affirm the schedule using the clinician programmer or any other suitable device.

In optional step 608, it is determined whether the patient or clinician (or both) affirm or accept the schedule. If no, then the procedure returns to step 602 or ends. If yes, then in step 610, the patient is stimulated according to the schedule.

It will be understood that each block of the flowchart illustration, and combinations of blocks in the flowchart illustration and methods disclosed herein, can be implemented by computer program instructions. These program instructions may be provided to a processor to produce a machine or engine, such that the instructions, which execute on the processor, create means for implementing the actions specified in the flowchart block or blocks or engine disclosed herein. The computer program instructions may be executed by a processor to cause a series of operational steps to be performed by the processor to produce a computer implemented process. The computer program instructions may also cause at least some of the operational steps to be performed in parallel. Moreover, some of the steps may also be performed across more than one processor, such as might arise in a multi-processor computing device. In addition, one or more processes may also be performed concurrently with other processes, or even in a different sequence than illustrated without departing from the scope or spirit of the invention.

The computer program instructions can be stored on any suitable computer-readable medium including, but not limited to, RAM, ROM, EEPROM, flash memory or other memory technology, CD-ROM, digital versatile disks ("DVD") or other optical storage, magnetic cassettes, magnetic tape, magnetic disk storage or other magnetic storage devices, or any other medium which can be used to store the desired information and which can be accessed by a computing device. The computer program instructions can be stored locally or nonlocally (for example, in the Cloud).

The above specification and examples provide a description of the arrangement and use of the invention. Since many embodiments of the invention can be made without departing from the spirit and scope of the invention, the invention also resides in the claims hereinafter appended.

What is claimed as new and desired to be protected is:

1. A method for modifying stimulation by a stimulation system comprising a stimulation device implanted in a patient, the method comprising:

identifying, by the stimulation system and over a period of time, a trend in manual adjustment of the stimulation in response to a trigger event;

defining a schedule for the adjustment of the stimulation based on the identified trend;

automatically, or with affirmation by the patient or a clinician, directing the adjustment of the stimulation according to the schedule; and stimulating the patient according to the schedule to achieve a therapeutic effect.

2. The method of claim 1, wherein the trend comprises a trend in manual adjustment of the stimulation at a particular time of day.

3. The method of claim 1, wherein the trend comprises a trend in manual adjustment of the stimulation in response to administration of medication.

4. The method of claim 1, wherein the trend comprises a trend in manual adjustment of the stimulation in response to a determination that the patient is engaging in a specified activity.

5. The method of claim 1, wherein the trend comprises a trend in manual adjustment of the stimulation in response to a change in a symptom of a disease or disorder or in a therapeutic effect or a side effect of stimulation.

6. The method of claim 5, further comprising detecting the change when the change comprises an increase or decrease for at least a predetermined period of time of at least one measured indicator.

7. The method of claim 5, further comprising detecting the change when the change comprises an increase or decrease by a predetermined magnitude of at least one measured indicator.

8. The method of claim 5, further comprising detecting the change using a sensor disposed on or within the patient.

9. The method of claim 5, wherein the symptom or side effect is dyskinesia.

10. The method of claim 5, wherein the symptom or side effect is freezing of gait.

11. The method of claim 1, further comprising receiving, at different times, each of the adjustments of the stimulation.

12. The method of claim 11, wherein the trend comprises a trend in manual adjustment of the stimulation in response to a change in a symptom of a disease or disorder or in a therapeutic effect or a side effect of stimulation.

13. The method of claim 12, further comprising logging the change into a memory of the stimulation system.

14. The method of claim 13, wherein the logging the change further comprises logging a time of the change into the memory of the stimulation system.

15. The method of claim 14, further comprising logging whether the adjustment of the stimulation is successful in addressing the change.

16. The method of claim 11, wherein the trend comprises a trend in manual adjustment of the stimulation in response to administration of medication.

17. The method of claim 16, further comprising logging the administration of the medication into a memory of the stimulation system.

18. The method of claim 17, wherein the logging further comprises logging a time of the administration of the medication into the memory of the stimulation system.

* * * * *